(12) United States Patent
Guevremont et al.

(10) Patent No.: US 6,770,875 B1
(45) Date of Patent: Aug. 3, 2004

(54) APPARATUS AND METHOD FOR DESOLVATING AND FOCUSSING IONS FOR INTRODUCTION INTO A MASS SPECTROMETER

(75) Inventors: Roger Guevremont, Gloucester (CA); Randy Purves, Gloucester (CA)

(73) Assignee: National Research Council Canada, Ottawa (CA)

( * ) Notice: Subject to any disclaimer, the term of this patent is extended or adjusted under 35 U.S.C. 154(b) by 0 days.

(21) Appl. No.: 09/762,239

(22) PCT Filed: Aug. 5, 1999

(86) PCT No.: PCT/CA99/00715

§ 371 (c)(1),
(2), (4) Date: Jun. 28, 2001

(87) PCT Pub. No.: WO00/08455

PCT Pub. Date: Feb. 17, 2000

Related U.S. Application Data

(63) Continuation of application No. 09/321,820, filed on May 28, 1999, now Pat. No. 6,504,149.
(60) Provisional application No. 60/095,481, filed on Aug. 5, 1998.

(30) Foreign Application Priority Data

Jan. 29, 1999 (CA) .............................................. 2260572

(51) Int. Cl.[7] .............................................. H01J 49/04
(52) U.S. Cl. ........................ 250/288; 250/281; 250/282
(58) Field of Search ................................. 250/282, 288, 250/281

(56) References Cited

U.S. PATENT DOCUMENTS

| | | | |
|---|---|---|---|
| 3,668,383 A | | 6/1972 | Carroll |
| 4,855,595 A | | 8/1989 | Blanchard |
| 5,420,424 A | * | 5/1995 | Carnahan et al. ........... 250/281 |
| 5,686,726 A | * | 11/1997 | Fenn et al. ................. 250/281 |
| 5,723,861 A | | 3/1998 | Carnahan et al. |
| 5,736,739 A | | 4/1998 | Uber et al. |

(List continued on next page.)

FOREIGN PATENT DOCUMENTS

| | | |
|---|---|---|
| WO | WO 00/63949 A1 | 10/2000 |
| WO | WO 01/22049 A2 | 3/2001 |

OTHER PUBLICATIONS

Buryakov, I. A., Krylov, E. V., Nazarov, E. G., and Rasulev, U. K., A new method of separation of multi–atomic ions by mobility at atmospheric pressure using a high–frequency amplitude–asymmetric strong electric field, Int. J. Mass Spectrom. Ion Processes, 128, 143 (1993).

Krylov, E. V., A method of reducing diffusion losses in a drift spectrometer, Tech. Phys., 44, 113 (1999).

Carnahan, B., Day S., Kouznetsov, V., Matyjaszczyk, M., and Tarassov, A., Field Ion Spectrometry—A New Analytical Technology for Trace Gas Analysis, Proceedings of the 41st Annual ISA Analysis Division Symposium, , Framingham, MA, pp. 85 (1996).

(List continued on next page.)

*Primary Examiner*—Jack Berman
(74) *Attorney, Agent, or Firm*—Freedman & Associates

(57) ABSTRACT

This invention provides an apparatus and method for desolvating and selectively transmitting and focussing ions, including ions produced by electrospray ionization (ESI), based on the ion focussing principles of high field asymmetric waveform ion mobility spectrometry (FAIMS), for introduction into a mass spectrometer. The ion focussing, trapping and desolvating effects of FAIMS, as identified by the inventors, provides high ion transmission efficiency and high sensitivity for the detection of ions. An apparatus comprising an ESI source, a FAIMS device and a mass spectrometer provides a way of desolvating and selectively transmitting highly solvated ions for introduction into a mass spectrometer for analysis.

46 Claims, 28 Drawing Sheets

U.S. PATENT DOCUMENTS

| | | | |
|---|---|---|---|
| 5,789,745 A | | 8/1998 | Martin et al. |
| 5,801,379 A | * | 9/1998 | Kouznetsov ................. 250/286 |
| 5,869,831 A | | 2/1999 | De La Mora et al. |
| 5,905,258 A | | 5/1999 | Clemmer et al. |
| 6,041,734 A | | 3/2000 | Raoux et al. |
| 6,124,592 A | * | 9/2000 | Spangler ...................... 250/282 |
| 6,162,709 A | | 12/2000 | Raoux et al. |
| 6,323,482 B1 | | 11/2001 | Clemmer et al. |
| 2001/0030285 A1 | * | 10/2001 | Miller et al. ................. 250/288 |
| 2001/0032929 A1 | | 10/2001 | Fuhrer |
| 2001/0032930 A1 | | 10/2001 | Gillig et al. |
| 2002/0070338 A1 | | 6/2002 | Loboda |
| 2002/0070339 A1 | | 6/2002 | Clemmer |

OTHER PUBLICATIONS

Riegner, D. E., Harden, C. S., Carnahan, B., and Day, S., Qualitative Evaluation of Field Ion Spectrometry for Chemical Warfare Agent Detection Proceedings of the 45th ASMS Conference on Mass Spectrometry and Allied Topics, , Palm Springs, California, pp. 473 (1997).

Spangler, G. E., Fundamental considerations for the application of miniature ion mobility spectrometry to field analytical applications, *Field Analytical Chemistry and Technology, 4,* 255 (2000).

Eiceman, G. A., Nazarov, E. G., Tadjikov, B., and Miller, R. A., Monitoring volatile organic compounds in ambient air inside and outside buildings with the use of a radio–frequency–based ion–mobility analyzer with a micromachined drift tube, *Field Anal. Chem. Tech., 4,* 297 (2000).

Miller, R. A., Eiceman, G. A., Nazarov, E. G., and King, A. T., A novel micromachined high–field asymmetric waveform–ion mobility spectrometer, Sensors Actuators B Chem, 67, 300 (2000).

Spangler, G. E., and Miller, R. A., Application of mobility theory to the interpretation of data generated by linear and RF excited ion mobility spectrometers, Int. J. Mass Spectrom., 214, 95–104 (2002).

Kiai, S. M. S., Confinement of ions in a radio frequency quadrople ion trap supplied with a periodic impulsional potential, Int. J. Mass Spectrom., 188, 177 (1999).

Kiai, S. M. S., Andre, J., Zerega, Y., Brincourt, G., and Catella, R., Study of a Quadrupole Ion Trap Supplied with a Periodic Impulsional Potential, Int. J Mass Spectrom. and Ion Processes, 107, 191 (1991).

Whetten, N. R., Macroscopic particle motion in quadrupole fields, J. Vac. Sci. Technol., 11, 515 (1974).

Buryakov, I. A., Kolomiets, Y. N., and Luppu, B. V., Detection of Explosive Vapors in the Air Using an Ion Drift Nonlinearity Spectrometer, J. Anal. Chem., 56, 336 (2001).

Krylov, E. V., Pulses of Special Shapes Formed on a Capacitive Load, Instruments and Experimental Techniques, 40, 628 (1997).

\* cited by examiner

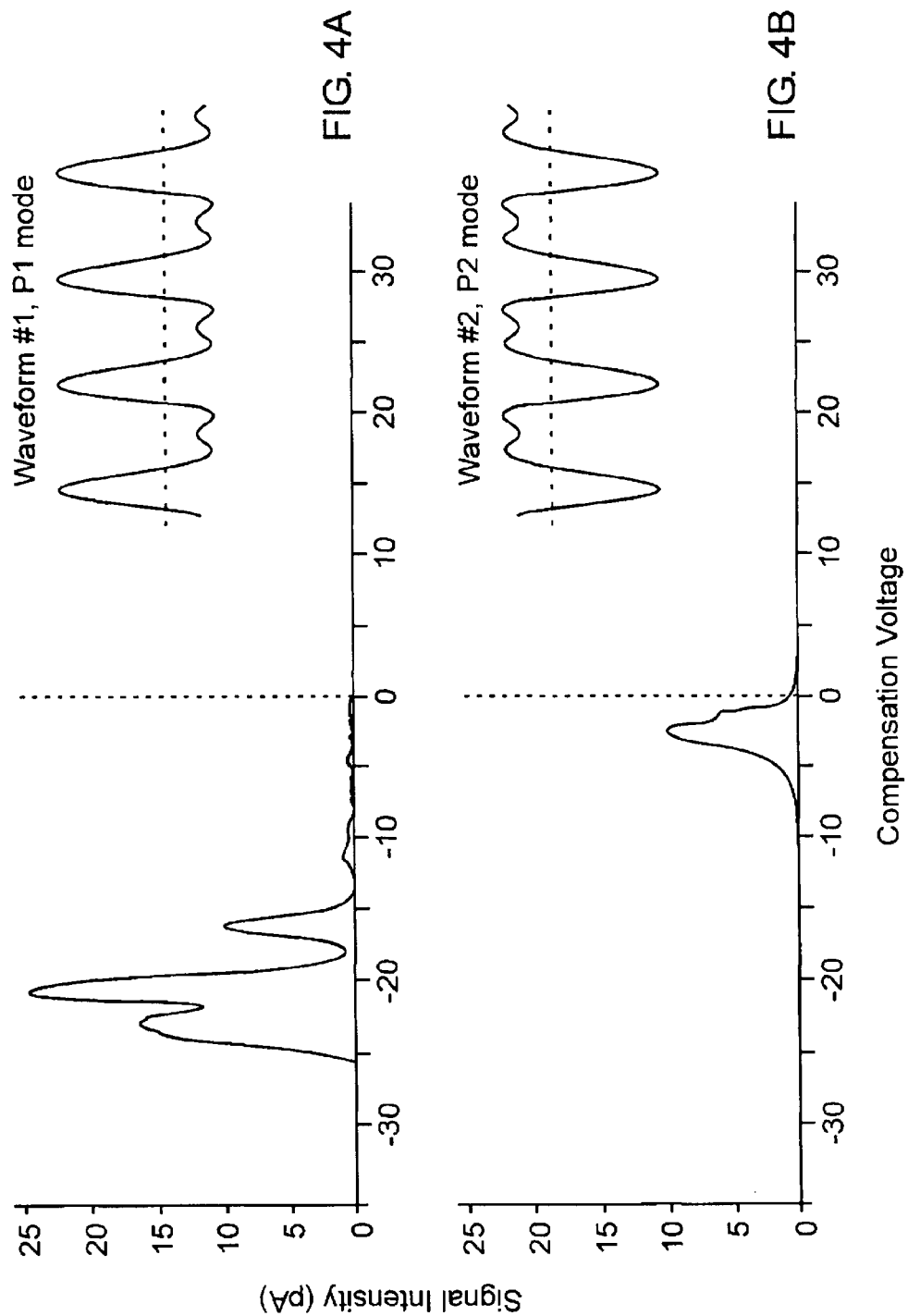

Timing Diagram for the Application of a High Frequency Asymmetric Waveform, a DC Voltage, and an Extraction Voltage The DV and CV Voltages are all applied to the center electrode. The Extraction voltage is applied to the grid located in front of the center electrode.

Details of the Asymmetric Waveform (time and amplitude not to scale)

APPARATUS AND METHOD FOR DESOLVATING AND FOCUSSING IONS FOR INTRODUCTION INTO A MASS SPECTROMETER

This application is a continuation of U.S. patent application Ser. No. 09/321,820 filed May, 28, 1999 now issued as U.S. Pat. No. 6,504,149 on Jan. 7, 2003, which claims the benefit of U.S. Provisional Application No. 60/095,481 filed Aug. 5, 1998. This application also claims the benefit of U.S. Provisional Application No. 60/095,481 filed Aug. 5, 1998.

FIELD OF THE INVENTION

The present invention relates to an apparatus and method for desolvating and selectively transmitting ions, based on the ion focussing principles of high field asymmetric waveform ion mobility spectrometry, for introduction into a mass spectrometer.

BACKGROUND OF THE INVENTION

High sensitivity and amenability to miniaturization for field-portable applications have helped to make ion mobility spectrometry an important technique for the detection of many compounds, including narcotics, explosives, and chemical warfare agents (see, for example, G. Eiceman and Z. Karpas, *Ion Mobility Spectrometry* (CRC. Boca Raton, Fla. 1994); and *Plasma Chromatography*, edited by T. W. Carr (Plenum, N.Y., 1984)). In ion mobility spectrometry, gas-phase ion mobilities are determined using a drift tube with a constant electric field. Ions are gated into the drift tube and are subsequently separated based upon differences in their drift velocity. The ion drift velocity is proportional to the electric field strength at low electric fields (e.g., 200 V/cm) and the mobility, K, which is determined from experimentation, is independent of the applied field. At high electric fields (e.g. 5000 or 10000 V/cm), the ion drift velocity may no longer be directly proportional to the applied field, and K becomes dependent upon the applied electric field (see G. Eiceman and Z. Karpas, *Ion Mobility Spectrometry* (CRC. Boca Raton, Fla. 1994); and E. A. Mason and E. W. McDaniel, *Transport Properties of Ions in Gases* (Wiley, N.Y., 1988)). At high electric fields, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry (see I. Buryakov, E. Krylov, E. Nazarov, and U. Rasulev. int. J. Mass Spectrom. Ion Proc. 128. 143 (1993); D. Riegner, C. Harden, B. Carnahan, and S. Day, Proceedings of the 45th ASMS Conference on Mass Spectrometry and Allied Topics, Palm Springs, Calif., 1–5 Jun. 1997, p. 473; B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85; and B. Carnahan and A. Tarassov, U.S. Pat. No. 5,420,424). Ions are separated in FAIMS on the basis of the difference in the mobility of an ion at high field $K_h$ relative to its mobility at low field K. That is, the ions are separated because of the compound dependent behaviour of $K_h$ as a function of the electric field. This offers a new tool for atmospheric pressure gas-phase ion studies since it is the change in ion mobility and not the absolute ion mobility that is being monitored.

An instrument based on the FAIMS concept has been designed and built by Mine Safety Appliances Company of Pittsburgh, Pa. ("MSA") for use in trace gas analysis. The MSA instrument is described in U.S. Pat. No. 5,420,424 and is available under the trade mark FIS (for Field Ion Spectrometer). While the use of the MSA instrument (and similar instruments based on the FAIMS concept) for trace gas analysis is known, the inventors believe that they have identified certain heretofore unrealized properties of these instruments which make them more versatile.

The realization of these properties has resulted in the development of an invention which is designed to extend the functionality of the MSA instrument (and similar instruments based on the FAIMS concept). A summary and detailed description of the present invention is provided below.

SUMMARY OF THE INVENTION

In a first aspect, the present invention provides an apparatus for selectively transmitting and determining the mass to charge ratio of ions, comprising:

a) at least one ionization source for producing ions;

b) a high field asymmetric waveform ion mobility spectrometer, comprising:
  i) an analyzer region defined by a space between first and second spaced apart electrodes, said analyzer region having a gas inlet at a first end and a gas outlet at a second end for providing, in use, a flow of gas through said analyzer region, said analyzer region having an ion inlet and an ion outlet, said ion inlet introducing a flow of ions produced by said ionization source into said analyzer region and said ion outlet allowing extraction of ions from said analyzer region;
  ii) an electrical controller connectable to said electrodes and capable of applying an asymmetric waveform voltage and a direct-current compensation voltage to selectively transmit a type of ion in said analyzer region between said electrodes at a given combination of asymmetric waveform voltage and compensation voltage; and c) a mass spectrometer having a sampler orifice, said sampler orifice being positioned proximate to said ion outlet to receive said selectively transmitted ions for analysis within said mass spectrometer.

Preferably, the first and second electrodes comprise curved electrode bodies and provide a non-constant electric field therebetween, said ions being selectively focussed in a focussing region created between said curved electrode bodies in said analyzer region.

In another aspect, the present invention provides apparatus for desolvating and selectively transmitting ions, comprising:

a) at least one electrospray ionization source for producing ions from a sample in liquid phase;

b) a high field asymmetric waveform ion mobility spectrometer, comprising:
  i) an analyzer region defined by a space between first and second spaced apart electrodes, said analyzer region being in communication with a gas inlet, a gas outlet, an ion inlet and an ion outlet, said ion inlet introducing a flow of said ions into said analyzer region, and said ion outlet allowing extraction of ions from said analyzer region;
  ii) a source of gas for providing a gas flow into said gas inlet and within said analyzer region, and out of said gas outlet, at least some of the gas flow being counter-current to said flow of ions being introduced at said ion inlet; and iii) an electrical controller connectable to said electrodes and capable of applying an asymmetric waveform voltage and a direct-current compensation voltage to selectively transmit a type of ion in an analyzer region between said electrodes at a given combination of asymmetric waveform voltage and compensation voltage.

In yet another aspect, the present invention provides an apparatus for selectively transmitting ions, comprising:

a) at least one electrospray ionization source for producing ions from a sample in liquid phase; and b) a high field asymmetric waveform ion mobility spectrometer, comprising:
  i) an analyzer region defined by a space between first and second spaced apart electrodes, said analyzer region being in communication with a gas inlet and a gas outlet for providing, in use, a gas flow through said analyzer region, an ion inlet and an ion outlet, said ion inlet introducing a flow of ions produced by said electrospray ionization source into said analyzer region, and said ion outlet allowing extraction of ions from said analyzer region; and
  ii) an electrical controller connectable to said electrodes and capable of applying an asymmetric waveform voltage and a direct-current compensation voltage to selectively transmit a type of ion in an analyzer region between said electrodes at a given combination of asymmetric waveform voltage and compensation voltage;

wherein, said electrospray ionization source is positioned external to said inner electrode so as reduce the effect of said asymmetric waveform voltage on said electrospray ionization source.

In yet another aspect, the present invention provides a method for desolvating and selectively focussing ions produced by electrospray ionization for introduction into a mass spectrometer, comprising the steps of:

a) providing at least one electrospray ionization source for producing ions from a sample in liquid phase;

b) providing an analyzer region defined by a space between first and second spaced apart electrodes, said analyzer region being in communication with a gas inlet, a gas outlet, an ion inlet and an ion outlet;

c) providing a gas flow into said gas inlet, and within said analyzer region, and out of said carrier gas outlet, at least some of said gas flow being counter-current to ions being introduced at said ion inlet;

d) providing an electrical controller connectable to said electrodes and capable of applying an asymmetric waveform voltage and a direct-current compensation voltage, to at least one of said electrodes;

e) adjusting said asymmetric waveform voltage and said compensation voltage to selectively focus a type of ion; and f) extracting said selectively transmitted ions from said analyzer region at said ion outlet for introduction into a sampler cone of a mass spectrometer.

BRIEF DESCRIPTION OF THE DRAWINGS

For a better understanding of the present invention, and by way of example, reference will now be made to the accompanying drawings, which show preferred embodiments of the present invention in which:

FIGS. 4A and 4B show compensation voltage spectra obtained under identical conditions except for the applied waveform being reversed in polarity between P1 mode and P2 mode;

FIGS. 8A(B) and 8A(C) show mass spectra obtained by setting the compensation voltage at two points of interest indicated by the vertical dashed lines in FIG. 8A(A);

FIG. 8B(B) shows a mass spectrum collected with the FAIMS not functioning (i.e., DV=0);

FIGS. 8B(C) and 8B(D) show mass spectra collected under different compensation voltage conditions for equine cytochrome C that illustrate the ion focussing concept compared with FIG. 8B(B);

DETAILED DESCRIPTION OF THE INVENTION

As an important preliminary note, although the discussion below generally uses the term "ion" to mean a charged atomic or molecular entity, the "ion" can be any electrically charged particle, solid or liquid, of any size. The discussion always refers to the "ion" as positively charged. However, all of the discussion in this disclosure is equally applicable to negative ions, but with the polarity of applied voltages being reversed.

Principles of FAIMS

The principles of operation of FAIMS have been described in Buryakov et. al. (see I. Buryakov, E. Krylov, E. Nazarov, and U. Rasulev, Int. J. Mass Spectrom. Ion Proc. 128. 143 (1993)) and are summarized here briefly. The mobility of a given ion under the influence of an electric field can be expressed by: $K_h(E)=K(1+f(E))$, where $K_h$ is the mobility of an ion at high field, K is the coefficient of ion mobility at low electric field and "f(E)" describes the functional dependence of the ion mobility on the electric field (see E. A. Mason and E. W. McDaniel, *Transport Properties of Ions in Gases* (Wiley, N.Y., 1988); and I. Buryakov, E. Krylov, E. Nazarov, and U. Rasulev, Int. J. Mass Spectrom. Ion Proc. 128. 143 (1993)).

Figure 1:
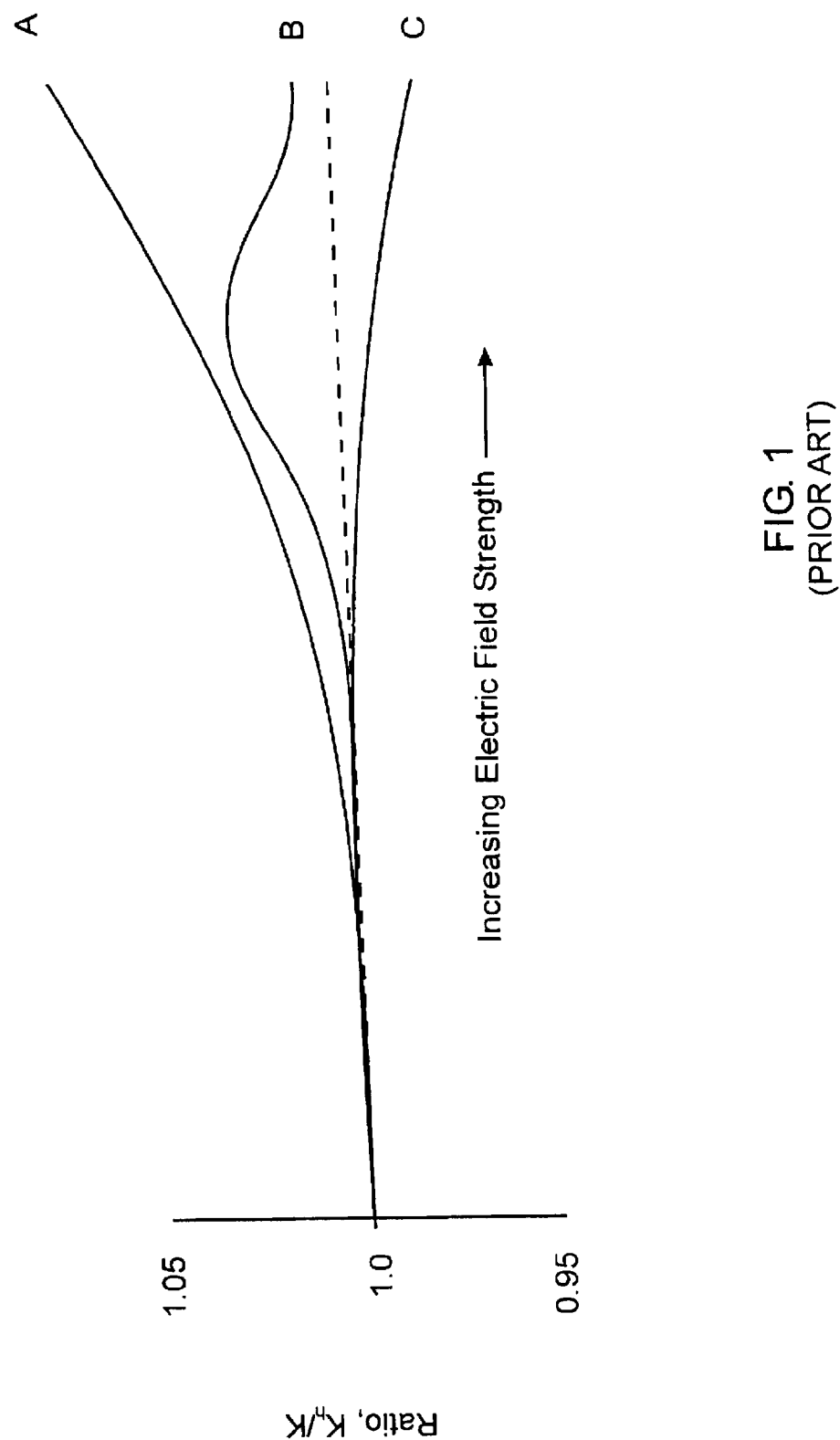
FIG. 1 shows three possible examples of changes in ion mobility as a function of the strength of an electric field.

Referring to FIG. 1, three examples of changes in ion mobility as a function of the strength of an electric field are shown: the mobility of type A ions increases with increasing electric field strength; the mobility of type C ions decreases; and the mobility of type B ions increases initially before decreasing at yet higher fields. The separation of ions in FAIMS is based upon these changes in mobility at high electric fields.

Figure 2:
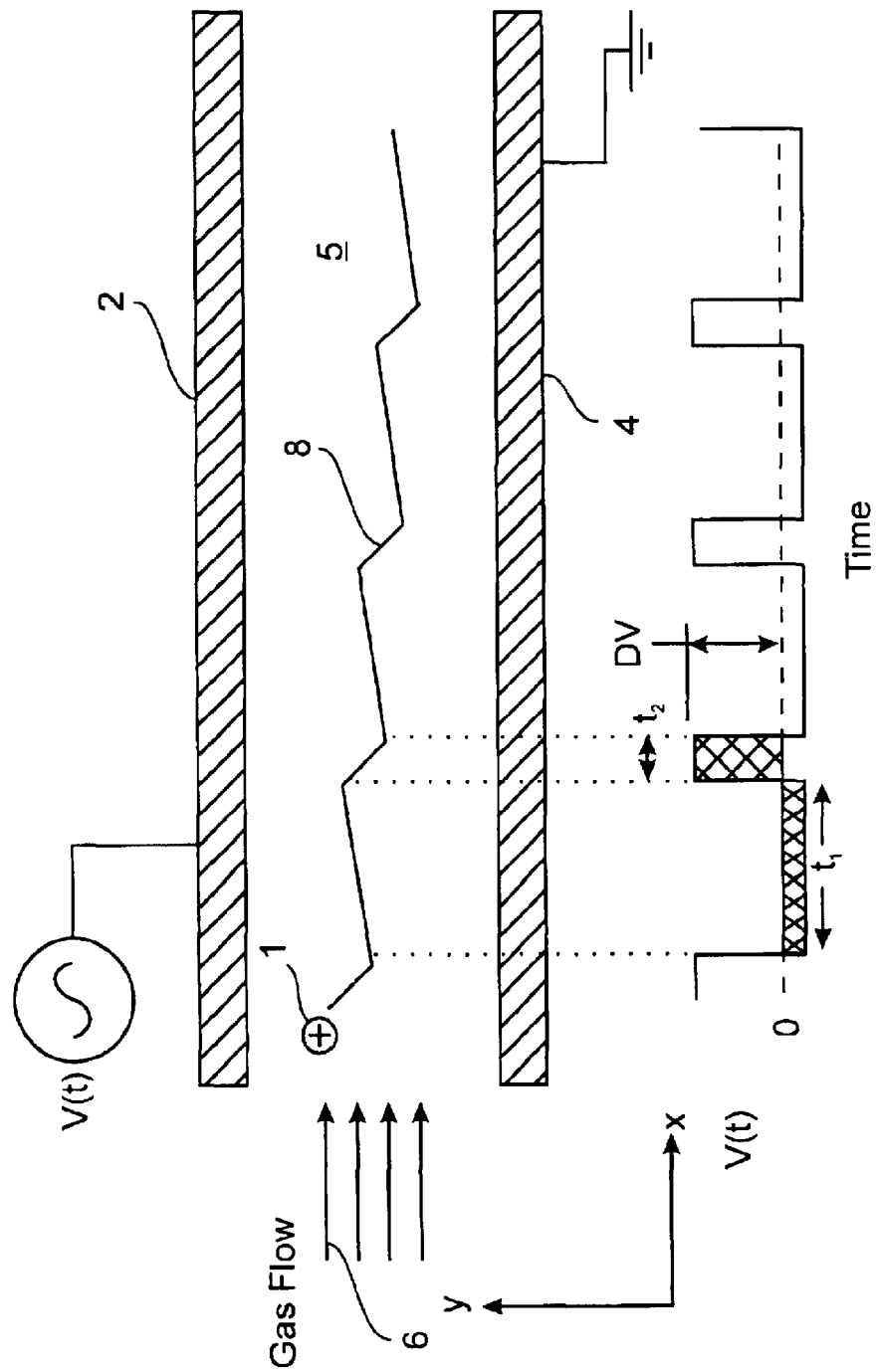
FIG. 2 illustrates the trajectory of an ion between two parallel plate electrodes under the influence of the electrical potential V(t)

Consider an ion 1, for example a type A ion shown in FIG. 1, that is being carried by a gas stream 6 between two spaced apart parallel plate electrodes 2, 4 as shown in FIG. 2. The space between the plates 2, 4 defines an analyzer region 5 in which the separation of ions may take place. The net motion of the ion 1 between the plates 2, 4 is the sum of a horizontal x-axis component due to a flowing stream of gas 6 and a transverse y-axis component due to the electric field between the plates 2, 4. (The term "net" motion refers to the overall translation that the ion 1 experiences, even when this translational motion has a more rapid oscillation superimposed upon it.) One of the plates is maintained at ground potential (here, the lower plate 4) while the other (here, the upper plate 2) has an asymmetric waveform, V(t), applied to it. The asymmetric waveform V(t) is composed of a high voltage component, V1, lasting for a short period of time $t_2$ and a lower voltage component, V2, of opposite polarity, lasting a longer period of time $t_1$. The waveform is synthesized such that the integrated voltage-time product (thus the field-time product) applied to the plate during a complete cycle of the waveform is zero (i.e., $V_1t_2+V_2t_1=0$); for example +2000 V for 10 μs followed by −1000 V for 20 μs. FIG. 2 illustrates the ion trajectory 8 (as a dashed line) for a portion of the waveform shown as V(t). The peak voltage during the shorter, high voltage portion of the waveform will be called the "dispersion voltage" or DV in this disclosure. During the high voltage portion of the waveform, the electric field will cause the ion 1 to move with a transverse velocity component $v_1=K_hE_{high}$, where $E_{high}$ is the applied field, and $K_h$ is the high field mobility under ambient electric field, pressure and temperature conditions. The distance travelled will be $d_1=v_1t_2=K_hE_{high}t_2$, where $t_2$ is the time period of the applied high voltage. During the longer duration, opposite polarity, low voltage portion of the waveform, the velocity component of the ion will be $v_2=KE_{low}$, where K is the low field ion mobility under ambient pressure and temperature conditions. The distance travelled is $d_2=v_2t_1=KE_{low}t_1$. Since the asymmetric waveform ensures that $(V_1t_2)+(V_2t_1)=0$, the field-time products $E_{high}t_2$ and $E_{low}t_1$ are equal in magnitude. Thus, if $K_h$ and K are identical, $d_1$ and $d_2$ are equal, and the ion 1 will be returned to its original position along the y-axis during the negative cycle of the waveform (as would be expected if both portions of the waveform were low voltage). If at $E_{high}$ the mobility $K_h$>K, the ion 1 will experience a net displacement from its original position relative to the y-axis. For example, positive ions of the type A shown in FIG. 1 will travel further during the positive portion of the waveform (i.e. $d_1$>$d_2$) and the type A ion 1 will migrate away from the upper plate 2 (as illustrated by the dashed line 8 in FIG. 2). Similarly, ions of type C will migrate towards the upper plate 2.

If an ion of type A is migrating away from the upper plate 2, a constant negative dc voltage can be applied to this plate 2 to reverse, or "compensate" for this transverse drift. This dc voltage, called the "compensation voltage" or CV in this disclosure, prevents the ion 1 from migrating towards either plate 2, 4. If ions derived from two compounds respond differently to the applied high electric fields, the ratio of $K_h$ to K may be different for each compound. Consequently, the magnitude of the compensation voltage CV necessary to prevent the drift of the ion toward either plate 2, 4 may also be different for each compound. Under conditions in which the compensation voltage CV is appropriate for transmission of one compound, the other will drift towards one of the plates 2, 4 and subsequently be lost. The speed at which the compound will move to the wall of the plates 2, 4 depends on the degree to which its high field mobility properties differ from those of the compound that will be allowed to pass under the selected condition. A FAIMS instrument or apparatus is an ion filter capable of selective transmission of only those ions with the appropriate ratio of $K_h$ to K.

The term FAIMS, as used in this disclosure, refers to any device which can separate ions via the above described mechanism, whether or not the device has focussing or trapping behaviour.

Improvements to FAIMS

The FAIMS concept was first shown by Buryakov et. al. using flat plates as described above. Later, Carnahan et. al. improved the sensor design by replacing the flat plates used to separate the ions with concentric cylinders (see B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85; U.S. Pat. No. 5,420,424 issued to Carnahan et al.). The concentric cylinder design has several advantages including higher sensitivity than the flat plate configuration (see R. W. Purves, R. Guevremont, S. Day, C. W. Pipich, and M. S. Matyjaszczyk, Rev. Sci. Instrum., 69, 4094 (1998)).

As mentioned earlier, an instrument based on the FAIMS concept has been built by Mine Safety Appliances Company (MSA). The MSA instrument uses the concentric cylinder design and is described further below. (For the purposes of this disclosure, the MSA instrument is referred to as FAIMS-E, where E refers to an electrometer or electric current detection device.)

One previous limitation of the cylindrical FAIMS technology (see D. Riegner, C. Harden, B. Carnahan, and S. Day, Proceedings of the 45th ASMS Conference on Mass Spectrometry and Allied Topics, Palm Springs, Calif., 1–5 Jun. 1997, p. 473; and B. Carnahan, S. Day, V. Kouznetsov, M. Matyjaszczyk, and A. Tarassov, Proceedings of the 41st ISA Analysis Division Symposium, Framingham, Mass., 21–24 Apr. 1996, p. 85) was that the identity of the peaks appearing in the FAIMS-E CV spectra could not be unambiguously confirmed due to the unpredictable changes in $K_h$ at high electric fields.

Thus, one way to extend the capability of instruments based on the FAIMS concept, such as the FAIMS-E instrument, is to provide a way to determine the make-up of the FAIMS-E CV spectra more accurately, for example, by introducing ions from the FAIMS-E device into a mass spectrometer for mass-to-charge (m/z) analysis.

In addition, it has been found that a modified FAIMS instrument, or any similar instrument, can be used in a new method of separating isomers and different confirmations of gaseous phase ions. The present invention is directed to a new method of separating isomers and different confirmations of ions and illustrates the method by several examples. Details of the method of the present invention are described below.

Electrospray Ionization

ESI is one of several related techniques that involves the transfer of ions (which can be either positively or negatively charged) from liquid phase into the gas-phase. Kebarle has described four major processes that occur in electrospray ionization (intended for use in mass spectrometry): (1) production of charged droplets, (2) shrinkage of charged droplets by evaporation, (3) droplet disintegration (fission), and (4) formation of gas-phase ions (Kebarle, P. and Tang, L. *Analytical Chemistry*, 65 (1993) pp. 972A–986A). In ESI, a liquid solution (e.g. 50/50 w/w water/methanol) is passed through a metal capillary (e.g., 200 $\mu$m outer diameter and 100 $\mu$m ID) which is maintained at a high voltage to generate the charged droplets, say +2000 V (50 nA) for example. The liquid samples can be pumped through at, say, 1 $\mu$L/min. The high voltage creates a very strong, non-constant electric field at the exit end of the capillary, which nebulizes the liquid exiting from the capillary into small charged droplets and electrically charged ions by mechanisms described by Kebarle and many others. Several related methods also exist for creating gas-phase ions from solution phase. Some examples of these methods include ionspray, which uses mechanical energy from a high velocity gas to assist in nebulization; thermospray, which applies heat instead of a voltage to the capillary; and nanospray, which uses small ID capillaries. In this disclosure, the term ESI is used to encompass any technique that creates gas-phase ions from solution.

Desolvation

In creating gas phase ions from a solution, some of the ions are created directly from the liquid, some of the ions are produced out of small droplets containing both the ions and solvent, and it is probable that many droplets are formed that do not produce any gas phase ions. Furthermore, the gas in which this complex mixture of ions, charged droplets, and non-charged droplets, are suspended also has a high concentration of solvent molecules. If this gas is simply allowed to pass into a mass spectrometer for analysis, the resulting spectra are extremely 'poor quality' because of heavy solvation. In this context, poor quality means that a particular charge state of an ion is represented in several places in the mass spectrum (i.e. the mass to charge (m/z) scale). For example, if $MH^+$ is the solvent-free protonated ion, then this ion may also appear as $MH^+$, $M(H_2O)H^+$, $M(H_2O)_2H^+$, $M(H_2O)_3H^+$ and so on. If the solution also contains methanol (which is typically the case in ESI) a 'poor' spectrum will contain, in addition to the series of hydrated ions noted above, yet further such 'series' of ions containing methanol, and combinations of water and methanol such as $M(H_2O)_m(MeOH)nH^+$ (where m, n are integers 0 and higher). A 'good' quality spectrum will contain only $MH^+$, i.e. m and n will both be zero. A good quality spectrum is an important requirement especially in experiments involving pharmaceutical and biological applications where the sample often contains very large numbers of different compounds, and compounds like proteins which may appear in the mass spectrum at many charge/mass ratios. Solvated ions that appear in these spectra add to the overall background in the spectrum, decreases the capability of the instrumentation to detect small quantities of specific compounds. Thus, high efficiency desolvation is necessary in these types of applications.

Currently, two methods are commonly used to achieve ion desolvation. The first method involves the use of what is referred to as a "curtain gas" (developed by MDS Health Group Limited, of Etobicoke, Ontario). In this method the orifice into the vacuum of a mass spectrometer is protected by a curtain of gas which is travelling in a direction different from that of the arriving ions. This curtain of gas has the effect of removing water and solvent from the gas adjacent to the orifice leading into the vacuum. A second method called the "heated capillary" method (used by Hewlett Packard Company, of Palo Alto, Calif., and others), minimizes ion solvation by heating the gas and ions as they pass into the vacuum of a mass spectrometer via a narrow bore capillary tube.

Inventors' Experiments

Three important concepts that are referred to in this disclosure are ion focussing, ion trapping and desolvation. These concepts are explained below with reference to various experiments conducted by the inventors. To set the background for the discussion a modified version of the FAIMS-E device is first described.

A) Modified FAIMS-E

As a first step, the FAIMS-E device designed and built by Mine Safety Appliances Company was modified to permit the introduction of ions using ESI. The inventors believe that the coupling of an ESI source together with a FAIMS-E device is not obvious as it is known that ions produced by ESI have a high degree of solvation, and that a FAIMS-E device may not function properly when exposed to high levels of solvent vapour. The inventors have developed various practical embodiments of an apparatus that combines an ESI source together with a FAIMS device to show that such coupling is possible.

Figure 3A:
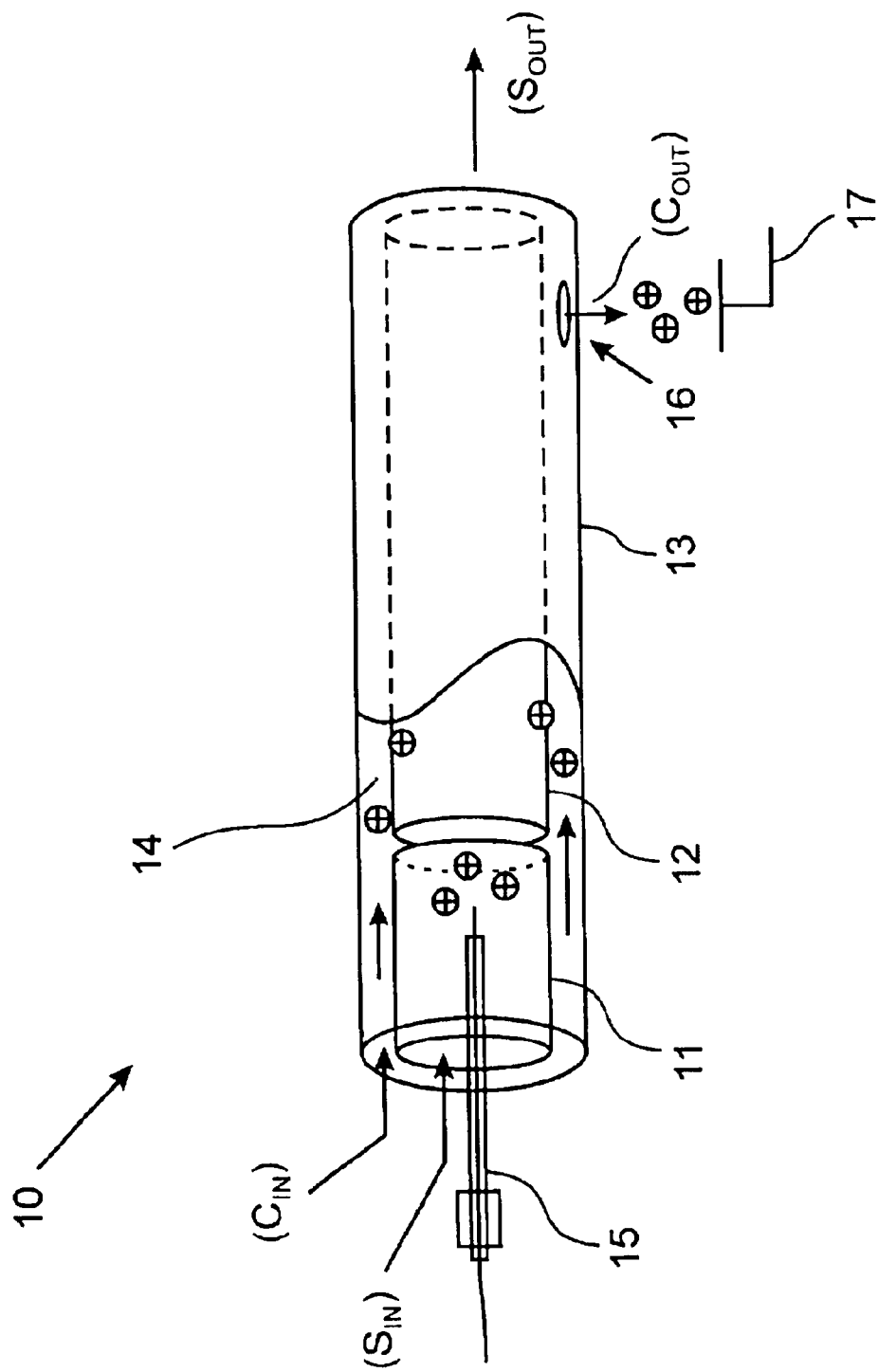
FIGS. 3A and 3B show schematically an embodiment of a modified FAIMS device.
Figure 3B:
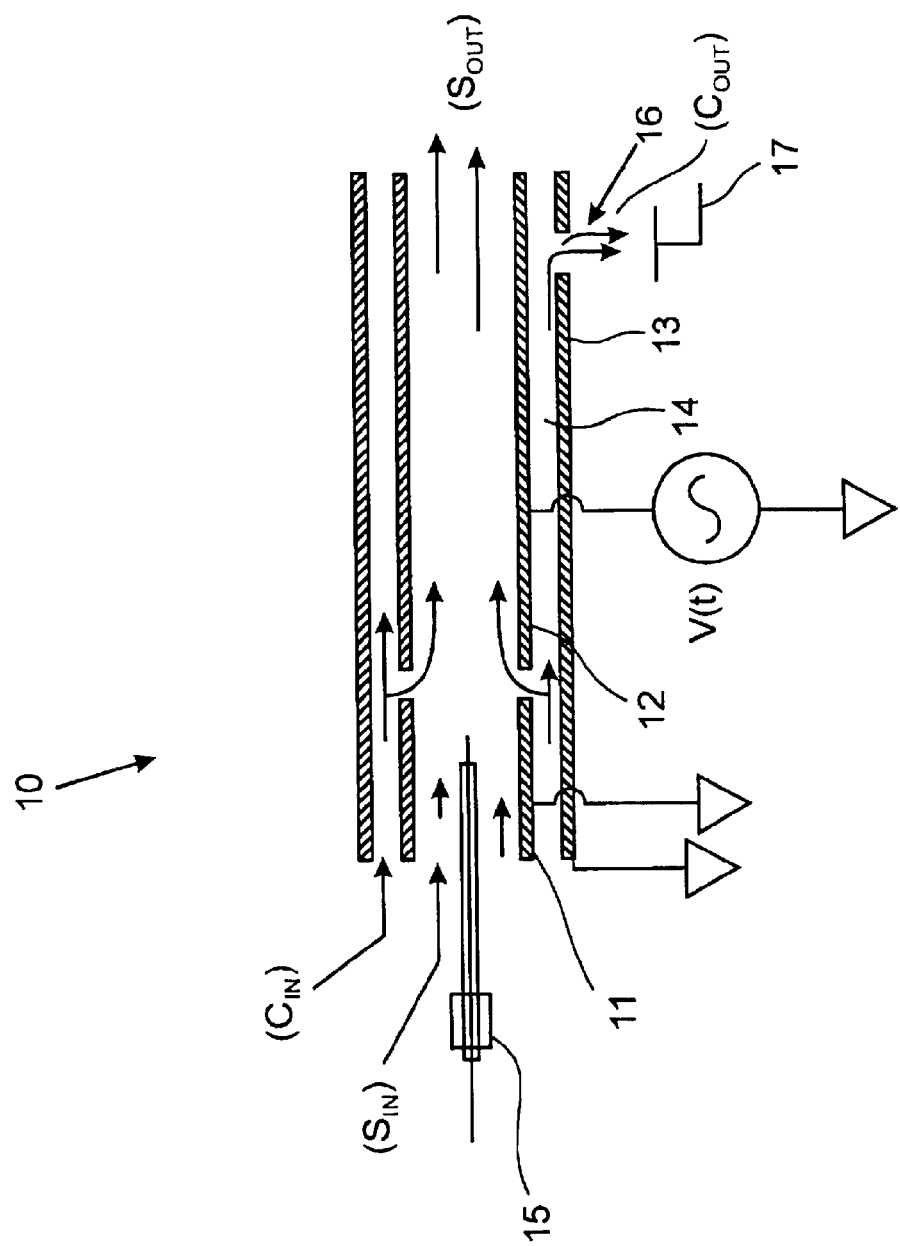

One example is the modified FAIMS-E device 10 shown schematically in 3-dimensional view in FIG. 3A and in cross section in FIG. 3B. The FAIMS-E apparatus 10 is composed of two short inner cylinders or tubes 11, 12 which are axially aligned and positioned about 5 mm apart, and a long outer cylinder 13 which surrounds the two inner cylinders 11, 12. The inner cylinders 11, 12 (12 mm inner diameter, 14 mm outer diameter), are about 30 mm and 90 mm long, respectively, while the outer cylinder 13 (18 mm inner diameter, 20 mm outer diameter) is about 125 mm long. Ion separation takes place in the 2 mm annular space of FAIMS analyzer region 14 between the long inner cylinder 12 and the outer cylinder 13. To produce ions using electrospray ionization (ESI), for introduction into the FAIMS analyzer region 14 of the FAIMS device, the metal capillary of the ESI needle 15 was placed along the central axis of the shorter inner cylinder 11, terminating about 5 mm short of the gap or ion inlet between the two inner cylinders 11, 12. The positioning of the ESI needle 15 shown in FIGS. 3(A) and 3(B) differs from the positioning of the ionization source found in the MSA FAIMS-E device in that the ESI needle 15 does not extend through the long inner cylinder 12 to which the asymmetric waveform V(t) is typically applied. By introducing the ESI needle 15 from the opposite end of the FAIMS-E, i.e. through the short inner cylinder 11, and not positioning the tip of the ESI needle 15 too close to the long inner cylinder 12, the performance of the ESI needle 15 is not compromised by the asymmetric waveform V(t), which would be the case if the ESI needle 15 was positioned within the long inner cylinder 12 (as disclosed in U.S. Pat. No. 5,420,424).

In an experiment conducted by the inventors, the solution was pumped through the metal capillary of the ESI needle 15, which was held between approximately +1500V and +2000V (e.g. 20 nA), at approximately 1 $\mu$l/min. Solutions that were used in this work consisted of an analyte which was dissolved in 0.1% acetic acid in a 1 to 1 (v/v) mixture of water/methanol. Note that the inventor' experiments with ESI have not been restricted to these chemicals/solvents alone; different solvents and chemicals can also be used. Several examples have been described in the literature.

As explained above, the FAIMS-E device 10 can be considered as an ion "filter", with the capability of selectively transmitting one type of ion out of a mixture. If a mixture of ions is presented continuously to the entrance of the FAIMS analyzer region 14, for example by an ESI needle 15, and the ions are carried along the length of the analyzer 14 by a flowing gas under conditions in which no voltages are applied to either the inner cylinder 12 or outer cylinder 13 (i.e. the electrodes are grounded), some finite level of transmission for every ion is expected, albeit without any separation.

It might be expected that the detected current of any selected ion in this mixture should never exceed the current for that ion when it is transmitted through the device 10 in the no-voltages condition. It might also be expected that application of high voltages (i.e. application of transverse fields, perpendicular to the gas flows) designed to yield ion separation should not increase the ion transmission, but should decrease transmission through collisions with the walls of the cylinders 12, 13. That is, the asymmetric waveform might effectively narrow the "width" of the FAIMS analyzer region 14, and therefore should decrease the ion transmission. However, contrary to this prediction, experiments conducted by the inventors and described in this disclosure have shown that the sensitivity of ion detection in the cylindrical geometry FAIMS-E 10 increases as the voltage amplitude of the asymmetric waveform V(t) is increased. As will be explained below, these unusual observations suggest that atmospheric pressure ion focussing is occurring in the FAIMS analyzer region 14.

The inventors believe that this phenomenon has many practical applications in the manipulation of ions at atmospheric pressure. For example, atmospheric pressure ion focussing could be used to improve the ion sampling efficiency of mass spectrometers that require transport of ions from atmospheric pressure to vacuum. These include atmospheric pressure ionization (API) spectrometers and atmospheric pressure sampling mass spectrometers, most notably those used for electrospray ionization. Details are provided further below.

Still referring to FIGS. 3A and 3B, four gas connections to the FAIMS-E apparatus 10 are shown. Compressed gas (e.g. air or nitrogen) is passed through a charcoal/molecular sieve gas purification cylinder (not shown) into the FAIMS-E 10 through carrier in ($C_{in}$) and/or sample in ($S_{in}$) ports. The gas exits the FAIMS-E 10 via the carrier out ($C_{out}$) and/or sample out ($S_{out}$) ports. All four gas flow rates can be adjusted. Non-volatile analytes are typically introduced into the FAIMS-E 10 using an ESI needle 15. Alternatively, volatile analytes may be introduced into the FAIMS-E 10 through the $S_{in}$ line, and a portion may be ionized as the compound(s) pass by a corona discharge needle.

In both cases, positively charged ions, formed in the short inner cylinder 11 are driven radially outward by the electric field of the ionization needle, whereas neutrals travel through the center of the long inner cylinder 12 and exit via the $S_{out}$ port. Neutrals are prevented from entering the annular FAIMS analyzer region 14 by a portion of the $C_{in}$ flow which is directed radially inward through the 5 mm gap or ion inlet between the inner cylinders 11, 12, and exits via the $S_{out}$ port. This portion of the $C_{in}$ gas flow that travels radially inward is counter-current to the ions being driven radially outward and acts to reduce the solvation of the ions. In addition, the inventors believe that further desolvation may be occurring as certain solvated ions travel down the FAIMS analyzer region 14 and are made to oscillate rapidly by the application of V(t). This desolvation capability of the FAIMS-E apparatus 10, as recognized by the inventors, is very important since it permits the collection of high quality electrospray CV spectra and mass spectra, without the use of other desolvation techniques, such as the use of a curtain gas, or the use of a heated capillary tube, both mentioned earlier.

Still referring to FIGS. 3A and 3B, the outer cylinder 13 of the FAIMS-E apparatus 10, and the shorter inner cylinder 11, are typically held at an adjustable electrical potential ($V_{FAIMS}$). $V_{FAIMS}$ is usually ground potential in FAIMS-E. During operation, a high frequency high voltage asymmetric waveform is applied to the long inner cylinder 12 to establish the electric fields between the inner and outer cylinders 12, 13. In addition to this high frequency (e.g., 210 kHz) high voltage waveform a dc offset voltage (i.e. the compensation voltage CV added to FAIMS) is applied to the long inner cylinder 12. This leads to the separation of ions in the FAIMS analyzer region 14 in the manner discussed earlier.

Still referring to FIGS. 3A and 3B, some of the ions produced by the ionization source are carried by the gas stream along the length of the annular space between the outer cylinder 13 and the long inner cylinder 12, also referred to as the FAIMS analyzer region 14. If the combination of dispersion voltage (DV) and CV are appropriate, and the ion is not lost to the tube walls, a series of opening or ion outlets 16 near the downstream end of the outer cylinder 13 allow the ions to be extracted to an electrical current detector 17 which is biased to about −100 V. (Note that here the carrier gas also exits from the ion outlet 16.)

Figure 4:
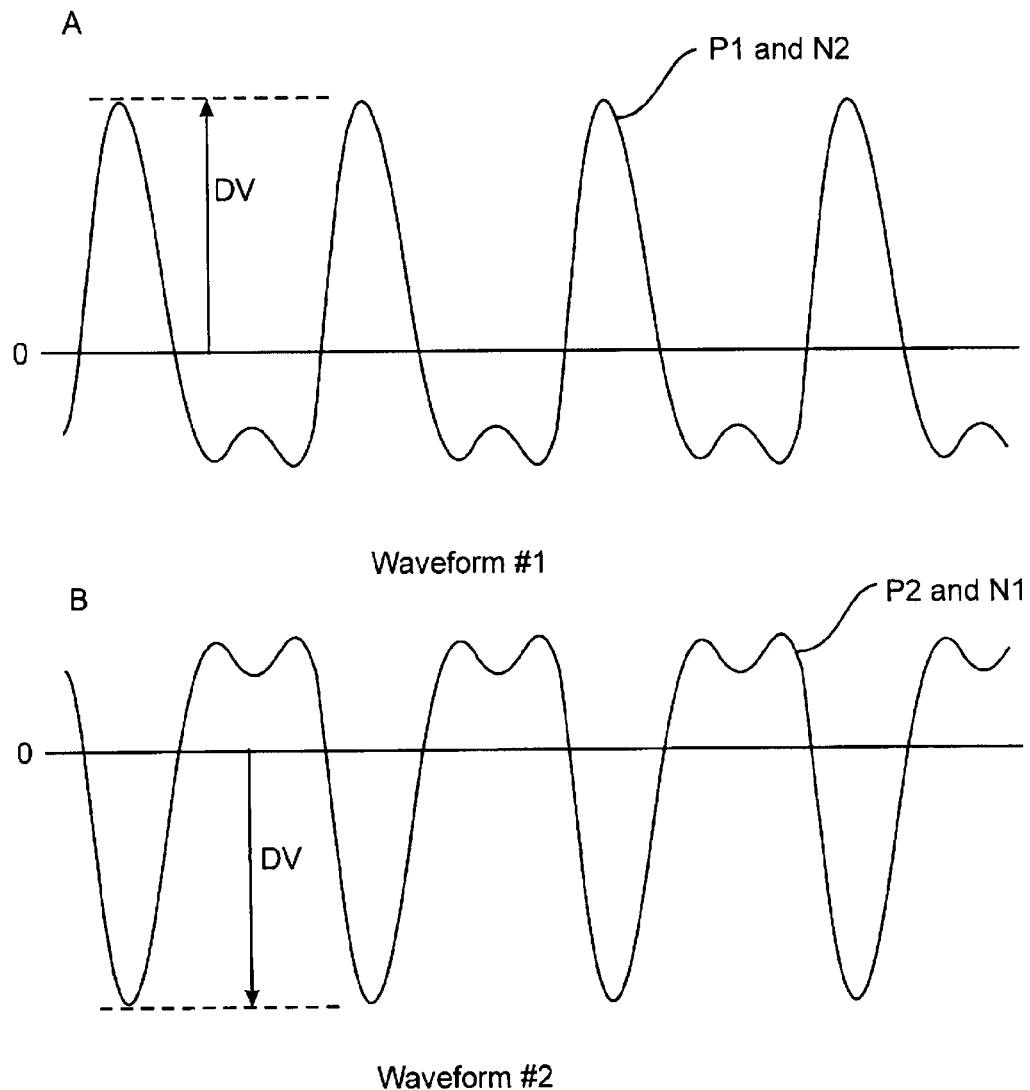
FIG. 4 illustrates two opposite waveform modes which may be used with the apparatus of FIGS. 3A and 3B.

In practice, the simplified square wave version of V(t) shown in FIG. 2 cannot be used because of the electrical power demands that such a wave would place on the waveform generator. The actual waveforms V(t) appear in FIG. 4. These waveforms are produced by the electronic addition of a sine wave and its harmonic of twice the frequency. As shown in FIG. 4, the FAIMS-E apparatus 10 operates using one of the two waveform modes (with the waveform applied to the inner cylinder). These reversed polarity waveform modes do not yield "reversed polarity" CV spectra as might be expected. This is because the reversal of polarity in this manner also creates a mirror image effect of the ion focussing behaviour of FAIMS. The result of such polarity reversal is that the ions are not focussed, but rather collide with the walls of the cylinders 12, 13. The mirror image of a focussing valley is a hill-shaped potential surface. (This characteristic, and the various "modes" of operation of FAIMS, is discussed further below.)

B) Ion Focussing

Figure 6A:
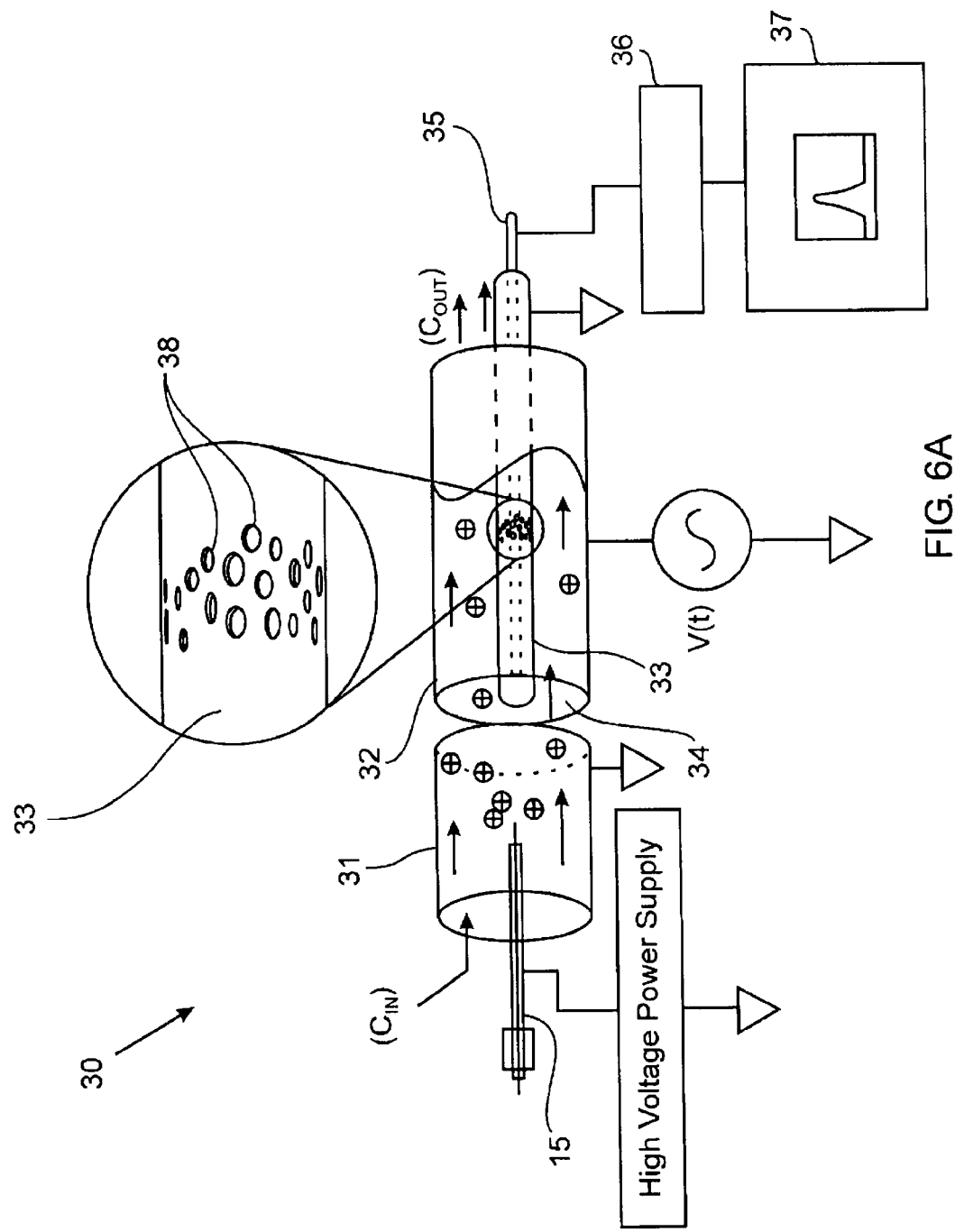
FIGS. 6A and 6B shows schematically a FAIMS apparatus for measuring the ion distribution in the analyzer region.
Figure 6B:
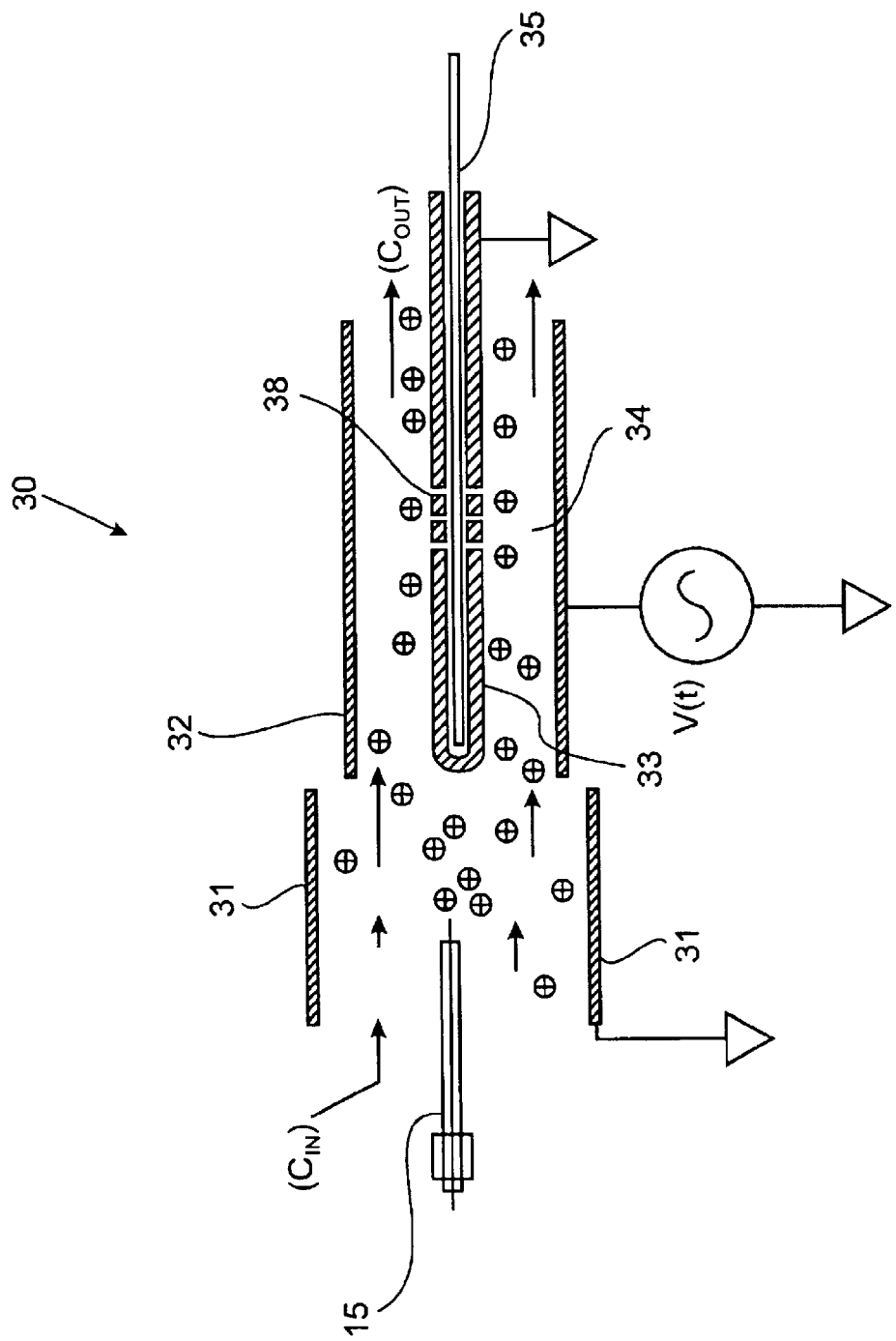

Referring now to FIGS. 6A and 6B, to demonstrate the focussing effect referred to above, a special FAIMS instrument was desired by the inventors and constructed to measure the ion distribution between the two cylinders (outer and inner cylinder) of a FAIMS device. This instrument will be referred to in this disclosure as the FAIMS-R1-prototype 30 and is illustrated schematically in FIGS. 6A and 6B. Ions were generated inside of an electrically grounded cylinder 31 approximately 35 mm long and 20 mm inside diameter (i,d). The tip of an ionization needle 15 was typically located near the center of this tube, and at least 15 mm from the end of the FAIMS analyzer region 34. The FAIMS analyzer region 34 in this embodiment is composed of an outer tube 32 which is 70 mm long and 6 mm i.d., and which surrounds a 2 mm o.d. inner shield electrode 33. The inner shield electrode 33 is an electrically grounded stainless steel tube which is closed at the end that faces the ionization needle 15. This inner electrode 33 surrounds, and shields, an electrically isolated conductor 35 passing into its center. This innermost conductor 35 (i.e the ion collector electrode) is it collector for ions, and is connected to a fist current amplifier or electrometer 36 (e.g. Keithly model 428) and a digital storage oscilloscope 37 (e.g. LeCroy model 9450).

In the system shown in FIGS. 6A and 6B, the ions which surround the inner electrode 33 are forced inwards by a pulsed voltage. These ions travel from the FAIMS analyzer region 34 to the innermost conductor 35 through a series of 50 µm holes 38 drilled through the inner shield electrode 33. The holes drilled in the inner shield electrode 33 are positioned about 2 cm from the end facing the ionization needle 15, and are spaced about 0.5 mm apart for a distance of 10 mm on one side of the inner shield electrode 33. The holes 38 drilled in the inner shield electrode 33 are located in this manner to minimize the variability in distance between the inner shield electrode 33 and the outer cylinder 32 in the vicinity of these holes 38. It was the inventor' objective to measure the ion abundance radial profiles of the ions located in the annular space (i.e. the FAIMS analyzer region 34) between the inner shield electrode 33 and the outer electrode 32 by pulsing the ions toward the inner shield electrode 33 and through the holes 38 and against the innermost ion collector electrode 35. The time-dependent distribution of ion arriving at the innermost conductor 35 is related to the physical,radial distribution of ions around the inner electrode 33. Excessive variation in the distance between the two cylinders 32, 33 would have increased the uncertainty of the ion arrival times at the innermost conductor 35, thus decreasing the spatial resolution of the measurements made with this device.

Figure 7:
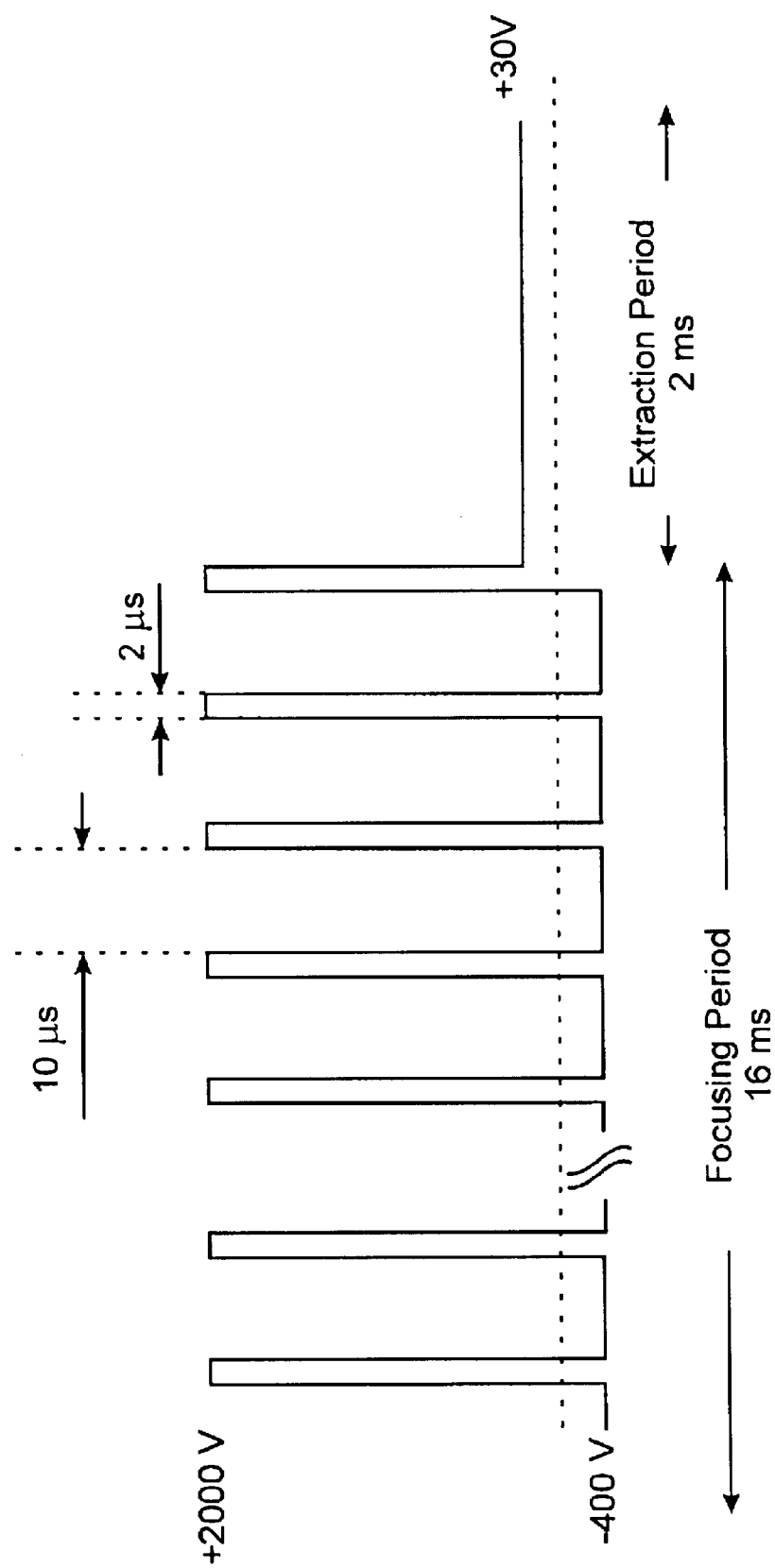
FIGS. 7 illustrates the high voltage, high; frequency asymmetric waveform applied to the FAIMS apparatus shown in FIGS. 6A and 6B.

Now referring to FIG. 7, the high voltage, high frequency asymmetric waveform V(t), applied to the FAIMS-R1-prototype of FIGS. 6A and 6B, is shown. The waveform is divided into two parts, the focussing period and the extraction period. The waveform was synthesized by an arbitrary waveform generator (e.g. Stanford Research Systems model DS340, not shown) and amplified by a pulse generator (e.g. Directed Energy Inc., model GRX-3.0K-H, not shown). The frequency of the waveform, and the relative duration of the high and low voltage portions of the waveform could easily be modified. Because of the high voltages, and steep rise-times of the square waves applied to this FAIMS-R1-prototype 30, the power consumption limits were severe, and waveforms in excess of about 1330 pulses (16 ms at 83,000 Hz) could not be delivered by this system without overheating electronic components of the high voltage pulse generator.

Note that, in the case of the FAIMS-R1-prototype 30, the high voltage, high frequency asymmetric waveform was applied to the outer cylinder 32 of the FAIMS-R1-prototype 30 shown in FIGS. 6A and 6B. Since all other forms of FAIMS discussed in this disclosure have the waveform applied to the inner tube or electrode, confusion may arise from the "polarity" of the waveform and the polarity of CV. In the FAIMS-R1-prototype 30 shown in FIGS. 6A and 6B, ions of type A (shown in FIG. 1) are focussed during application of the opposite polarity waveform and CV than that shown for the devices in FIGS. 3A, 3B, 5A and 5B. Nevertheless, for simplification, the polarity will be written to be the same as if the device was constructed in the same way as those of the more conventional configuration. In other words the ions transmitted during application of waveform #1 will appear with DV positive and with CV negative. (Please note, however, that the actual voltages used on the device in FIGS. 6A and 6B are DV negative and CV positive).

As was observed in the conventional parallel plate FAIMS apparatus described earlier (FIG. 2), the application of a high voltage asymmetric waveform V(t) will cause ions to migrate towards one of the FAIMS electrodes 2, 4 because of the changes in ion mobility at high electric fields (shown in FIGS. 1 and 2). This migration can be stopped by applying an electric field or compensation voltage CV in a direction to oppose the migration. For the FAIMS-R1-prototype 30 of FIGS. 6A and 6B, this CV was applied to the same electrode as the high voltage asymmetric waveform (i.e. the outer electrode 32), and was added to the waveform as a small dc bias (up to +50 V). At an appropriate combination of DV, and compensation voltage CV, a given ion will pass through the FAIMS device 30. The unit therefore acts like an ion filter. It is possible to fix conditions such that a single type of ion is isolated in the FAIMS analyzer 34 although a mixture flows uniformly out of the exit of the FAIMS device 30 although a mixture of ions are presented to the inlet of the FAIMS analyzer region 34.

The second part of the waveform shown in FIG. 7 (i.e. the extraction period) was used to pulse the ions out of the FAIMS analyzer region 34 between the outer electrode 32, and the inner shield electrode 33, (shown in FIGS. 6A and 6B). At the end of the focussing period, i.e. after 16 ms of waveform, the asymmetric waveform was replaced by a constant dc bias of approximately +30 V. This caused the ions from the annular space 34 between the outer electrode 32 and the inner shield electrode 33 to move in the direction of the inner shield electrode 33. A detector bias of −5 V, applied to innermost ion collector electrode 35, helped to carry the ions from the vicinity of the holes 38 in the inner shield electrode 33, through the holes 38 and into contact with the innermost ion collector electrode 35. The +30 V bias created an electric field of approximately 150 V/cm across the FAIMS analyzer region 34 and most ions located within this region 34 travelled across the 2 mm space in about 1 ms. The ion current due to the arrival of ions at the center inner shield electrode 33 can be predicted. For example, if only one type of ion, with mobility of 2.3 cm$^2$/V-s, e.g., $(H_2O)_nH^+$ at ambient temperature and pressure conditions, was located in the FAIMS analyzer region 34, and if this ion was distributed evenly in the space, an approximately square-topped signal lasting approximately 0.6 ms should be observed. Deviation from this expected ion arrival profile would suggest that the ions were distributed in non-uniform profile across the FAIMS analyzer region 34 between the outer and inner cylinders of the FAIMS device 30.

Still referring to FIGS. 6A, 6B, and 7, the FAIMS-R1-prototype 30 was operated as follows. A 2 L/min flow of purified air, Carrier Gas In (Cin), was passed into the cylinder 31 housing the ionization needle 15. Approximately 2000 V was applied to the needle 15, and the voltage was adjusted to produce a stable ionization current. The high voltage asymmetric waveform V(t) was applied to the outer FAIMS cylinder 32 for approximately 16 ms; this was followed by a 2 ms extraction pulse (FIG. 7). The ion current striking the innermost ion collecting electrode 35 was detected and displayed on a digital oscilloscope 37. A measurement would typically consist of 100 averaged spectra, collected at a rate of approximately 5 Hz. Many experimental parameters were varied, including gas flow rates, the voltages of the asymmetric waveform V(t), the dc voltage applied to the outer electrode CV, and the extraction voltage.

Figure 8:
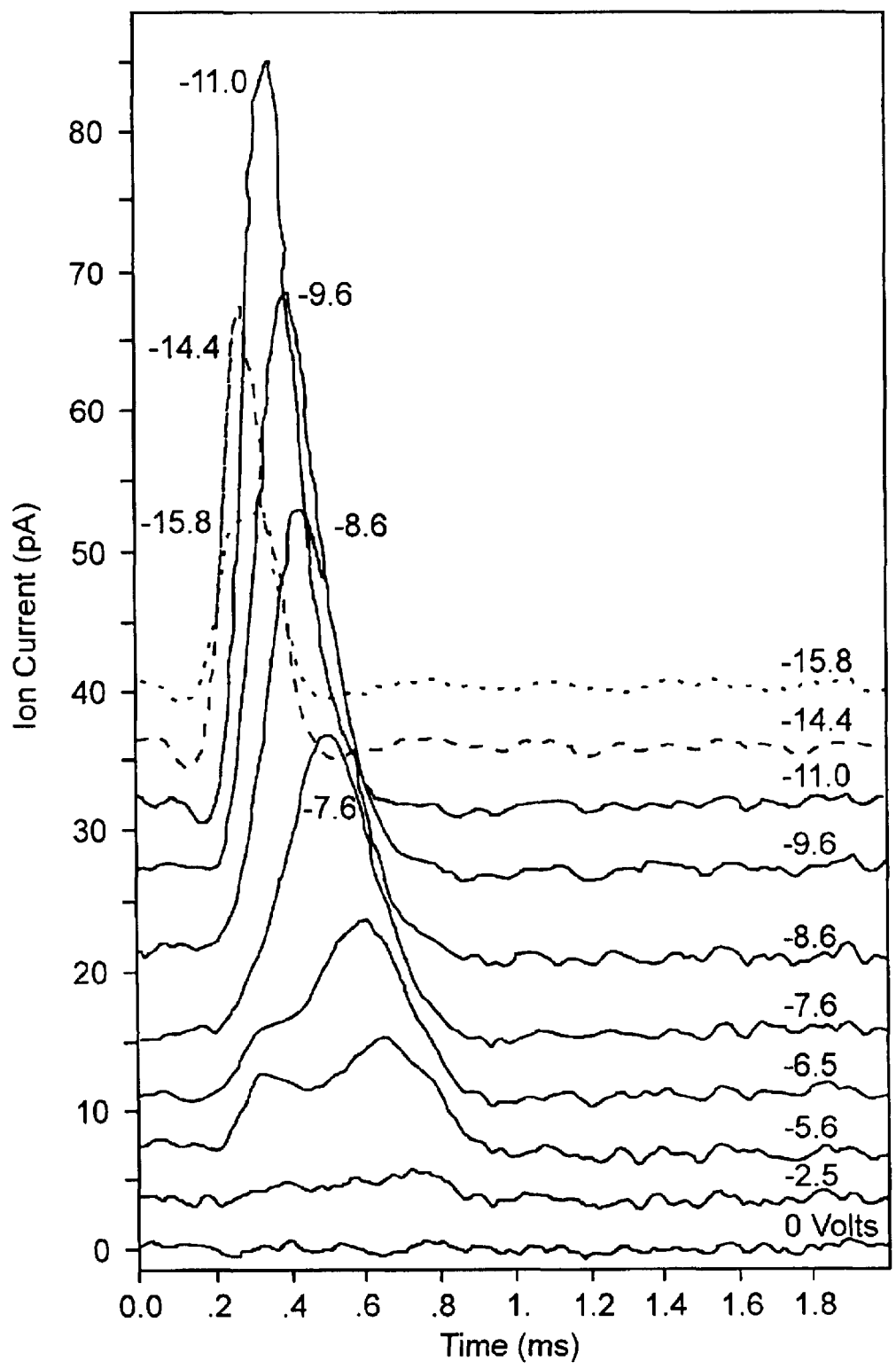
FIG. 8 illustrates varying ion arrival time profiles at the innermost ion collector electrode of the FAIMS apparatus in FIGS. 6A and 6B.

FIG. 8 illustrates the ion arrival times at the innermost ion collector electrode 35 observed by conducting these experiments. Each trace was recorded with 2500 V applied DV, but with variable CV voltages. As can be seen, during application of DV and CV, the radial distribution of ions is not uniform across the annular space of the FAIMS analyzer region 34. For example, at CV near −11 V, the ions are focussed into a narrow band near the inner electrode 33, and therefore are detected as a high intensity pulse occurring very early after the extraction voltage has been applied. At low CV, for example at −5.6 V, the ions are much more uniformly distributed between the walls of the concentric cylinders 32 33 making up the FAIMS analyzer region 34. When no electrical voltages are applied to the cylinders 32, 33, the radial distribution of ions should be approximately uniform across the FAIMS analyzer region 34 (data for this no-voltage experimental condition is not shown in this document). The experimental data shown in FIG. 8 is evidence that the ion focussing is indeed occurring in FAIMS instruments. This focussing results in the ions being focussed in a uniform "sheet" or band around the inner cylinder 33 within the FAIMS analyzer region 34. As mentioned previously, to the inventor' knowledge, this focussing effect has never been observed or explained previously.

C) 3-Dimensional Atmospheric Pressure Ion Trap

Taking the focussing effect a step further, the inventors believe they have developed a 3-dimensional atmospheric pressure ion trap, which is the subject of Canadian Patent Application No. 2,260,572 filed by the inventors Jan. 29, 1999 (now abandoned) and which is explained briefly here.

The gas flows between the cylinders of the FAIMS devices described above serve to carry the ions from one end of the device to the other end. In every case the action of the electric fields is perpendicular to the transporting motion of the gas flow. This is the reason the early devices were referred to as "transverse field" compensation ion mobility spectrometers. The inventors have carried out experiments in which the 2-dimensional ion focussing action of the FAIMS-E 10 and FAIMS-R1-prototype 30 was utilized together with a gas flow to form a 3-dimensional trap by ensuring that the ions are caught in a physical location in which the gas flows and the electrical fields are not perpendicular, but rather act in opposition to each other. This creates the situation in which the ion cannot progress in any direction whatsoever. This is the 3-dimensional atmospheric pressure ion trap. (An apparatus for trapping ions is shown in FIGS. 9, 11, 12, 13A and 13B and is described in more detail below. As shown in FIG. 3B, ion trapping occurs near the curved or spherical terminus of the inner electrode.)

Note that, in this disclosure, the term "ion focussing" is restricted to a 2-dimensional configuration. That is, if the ions are "focussed", they will be restricted to a sheet-like structure, and the thin, flat sheet surrounds the inner cylinder. For example, if ions are "focussed" around the external surface of a long metallic cylinder, this will mean that they are restricted to be within a cylindrical space (composed of the ions) which is coaxial to, or surrounding the metallic cylinder. This sheet of ions will extend as far as the cylinder, and all around it continuously. On the other hand, in this disclosure the term "ion trapping" is restricted to the condition that an ion cannot move freely in any direction in 3-dimensional space. This is more restrictive than "focussing", in which the ion is free to move anywhere in the 2-dimensions e.g. along the length of the cylinder described in the example noted above or around the cylinder at a fixed radius.

Three-dimensional ion traps for operation in vacuum chambers of mass spectrometers are well known, and several geometries exist. However, the mechanism and operation of these vacuum-ion-traps is vastly different from that of the atmospheric pressure (760 torr) version of the ion trap described in this disclosure. The physical geometry, the layout of the hardware components, and the electrical voltages applied in known 3-dimensional ion traps are in no way related to the present atmospheric version of the ion trap. To the inventor' knowledge, an atmospheric 3-dimensional ion trap has not been previously achieved.

It is also possible to operate a 3-dimensional ion trap in a compromised, near trapping condition so that ions can be focused into a smaller region in space. This is described further below in reference to FIGS. 13A–13C and 14A–14C.

D) Modes of Operation of FAIMS

The focussing and trapping of ions by the use of asymmetric waveforms has been discussed above. For completeness, the behaviour of those ions which are not focussed within the FAIMS analyzer region will be described here. As explained earlier, the ions which do not have the high field ion mobility properties suitable for focussing under a given set of DV, CV and geometric conditions will drift toward one or another wall of the device, as shown in FIG. 2. The rapidity with which they move to the wall depends on the degree to which their Kh/K ratio differs from that of the ion that might be focussed under the selected condition. At the very extreme, ions of completely the wrong property i.e. type A ion versus type C ion shown in FIG. 1, will be lost to the walls very quickly.

The loss of ions should be considered one more way. If an ion of type A (FIG. 1) is focussed at DV 2500 volts, CV −11 volts in a given geometry (for example, the FAIMS-E device of FIGS. 3A–3B), is it reasonable to expect that the ion will also be focussed if the polarity of DV and CV are reversed, i.e. DV of −2500 volts and CV of +11 volts (both applied to the inner electrode). It would seem that the reversal of polarity is a trivial exercise and the ion should be focussed, however, this is not observed. Instead, the reversal of polarity in this manner creates the mirror image effect of the ion focussing behaviour of FAIMS. The result of such polarity reversal is that the ions are not focussed, but rather are extremely rapidly rejected from the device, and collide with the walls of the cylinders 12, 13. The mirror image of a trapping valley, is a hill-shaped potential surface. The ions will slide to the center of the bottom of a trapping potential valley (2 or 3-dimensions), but will slide off of the top of a hill-shaped surface, and hit the wall of an electrode. This apparently anomalous behaviour is a consequence of the cylindrical geometry of the FAIMS-E.

This is the reason for the existence, in the FAIMS, of the independent "modes" called 1 and 2. In this disclosure, the FAIMS instrument is operated in four modes: P1, P2, N1, and N2. The "P" and "N" describe the ion polarity, positive (P) and negative (N). The waveform (FIG. 4, wave #1) with positive DV (where DV describes the peak voltage of the high voltage portion of the asymmetric waveform) yields spectra of type P1 and N2, whereas the reversed polarity (FIG. 4, wave #2, negative DV) waveform yields P2 and N1. The discussion thus far has considered positive ions but, in general, the same principles can be applied to the negative ions, as explained in the preliminary note to the Detailed Description Referring now to FIGS. 4A and 4B, CV spectra were collected under identical conditions, but the applied waveform was reversed in polarity (P1 and P2). The. CV was scanned in both the negative and positive polarity in each case. The ions of type A, FIG. 1, appear in mode P1 in the negative CV portion of the FIG. 4A, whereas ions with type C behaviour, FIG. 1, only appear in mode P2 and are seen in the negative CV portion of FIG. 4B. Mass spectrometry was used to eliminate the possibility of incorrectly identified ions.

E) Spectra generated using ESI-FAIMS-MS

The FAIMS acts as an ion filter and can be used in the four distinct modes described above. In this disclosure we discuss positive ions (a similar argument can be made for negative ions). In particular, two examples are discussed: one illustrates the desolvation capabilities of P1 mode (using CsCl), the other illustrates the desolvation capabilities of P2 mode (using equine cytochrome c). In general, small analytes (molecular weight is ~300 or less) are observed in P1 spectra and larger analytes, such as proteins, are observed in P2 mode. Both CV spectra and mass spectra are shown for these two examples. We emphasize that several solutions of analytes have been analyzed using this technique and that these are only two examples to show the capabilities of desolvation.

Figure 8A:
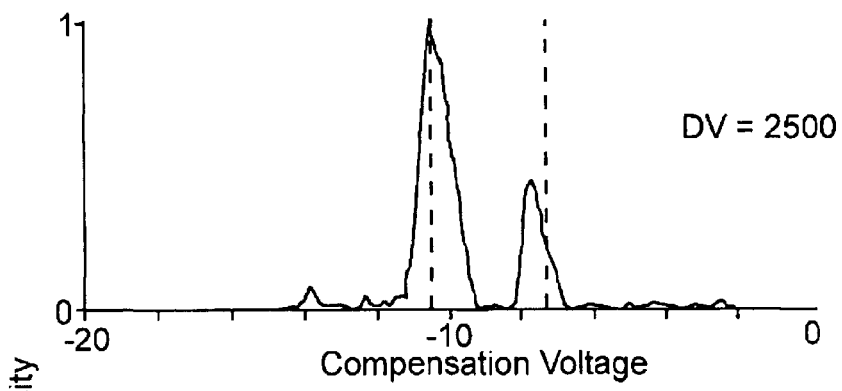
FIG. 8A(A) shows a compensation voltage spectrum for CsCl in an ion filtering experiment.
Figure 8A:
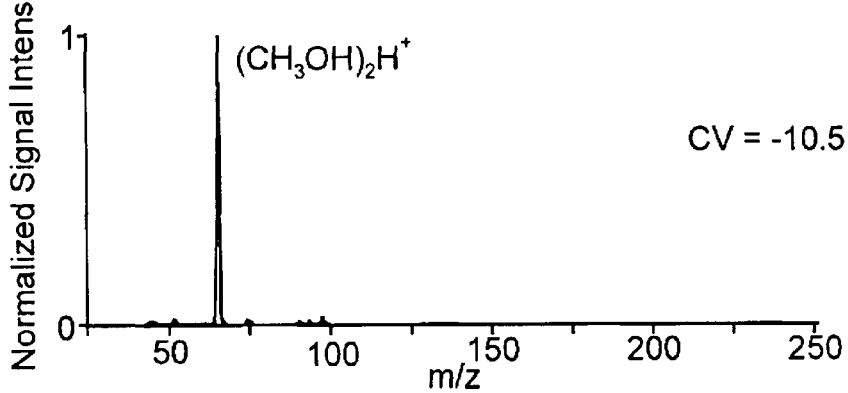
Figure 8A:
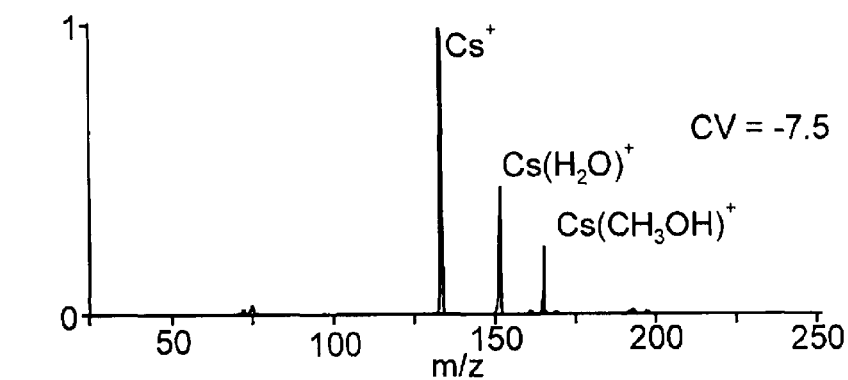

FIG. 8A(A) shows a total ion current CV-spectrum CsCl (m/z range from 30 to 300 was monitored as a function of CV) when the DV was set to 2500 V using P1 mode. Mass spectra of the two distinct peaks in FIG. 8A(A) were obtained. FIGS. 8A(B) and 8A(C) were collected by setting the compensation voltage to −10.5 V and −7.5 V, respectively (indicated by the vertical dashed lines in FIG. 8A(A)). The mass spectrum in FIG. 8A(B) is dominated by the peak at m/z 65 which is $[CH_3OH]_2H^+$ (from the solvent). FIG. 8A(C) shows the mass spectrum for the analyte of interest ($Cs^+$) with relatively little residual solvation (compared to spectra collected without any desolvation, not shown). The bare $Cs^+$ ion is the most abundant peak (m/z 133) in this mass spectrum, $Cs[H_2O]^+$ (m/z 151) and $Cs[CH_3OH]^+$ (m/z 165) are also present.

Figure 8B:
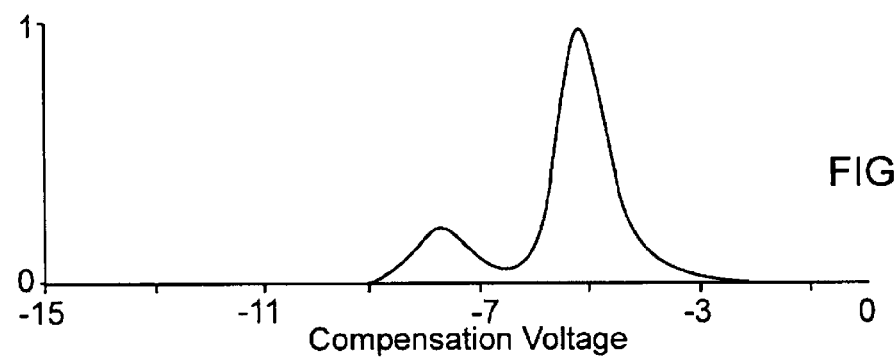
FIG. 8B(A) shows an example of ions separated by FAIMS using equine cytochrome C.
Figure 8B:
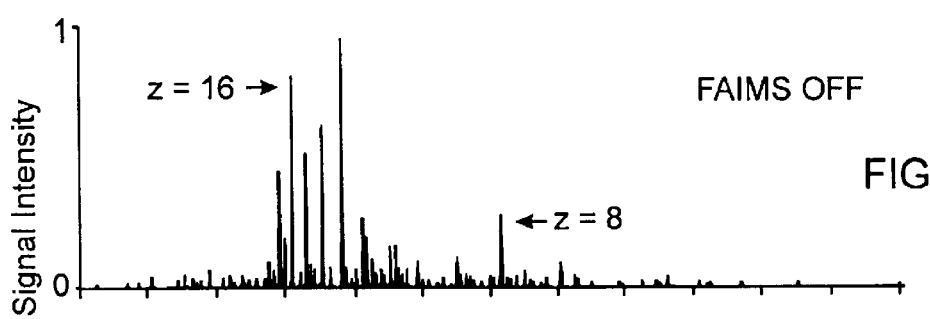
Figure 8B:
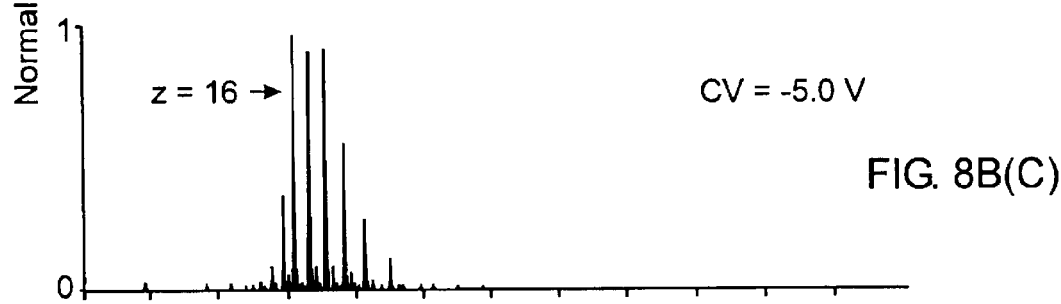
Figure 8B:
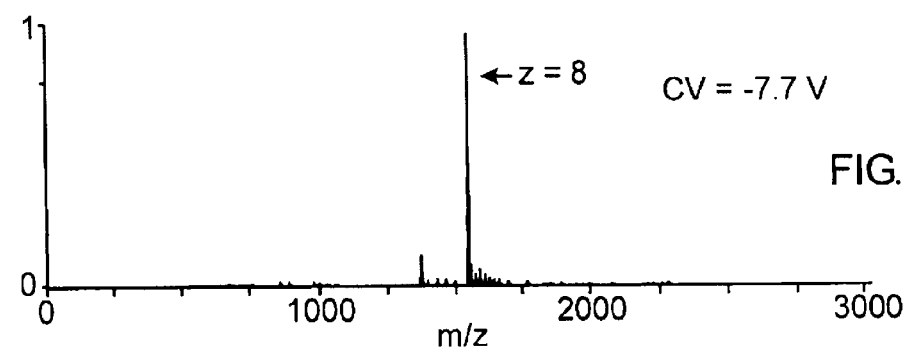

FIG. 8B(A)–8B(D) illustrates by way of example the FAIMS focussing concept described above using a protein, equine cytochrome c (MW=12360). FIG. 8B(A) shows the CV-spectrum that is obtained by selected ion monitoring the m/z ratio of the charge states of cytochrome c from $5^+$ to $20^+$ (i.e., 2473.0 (z=5), 2061.0 (z=6), 1766.7 (z=7), ..., 619.0 (z=20)) while scanning the CV. In obtaining this spectrum, the FAIMS was operated in P2 mode with a DV of 3300 V. Mass spectra collected under three different conditions are shown in FIGS. 8B(B), 8B(C) and 8B(D).

The mass spectrum shown in FIG. 8B(B) was collected without the application of the high voltage asymmetric waveform to the FAIMS-MS (note that the IS-CV-spectrum in FIG. 8B(A) was collected with the waveform applied). Since the asymmetric waveform (and thus DV) was not applied, the ions were not drifting toward either electrode, and the compensation voltage (CV) was nearly zero (−0.2 volts) in order to optimally transmit ions through the (non-functioning) FAIMS hardware. This spectrum is only shown for comparison to the conditions shown in FIGS. 8B(C) and 8B(D) in which the DV and CV were applied to the FAIMS. The spectra shown in FIGS. 8B(C) and 8B(D) are of much higher quality, and sensitivity and signal-to-noise ratio (S/N) than that shown in FIG. 8B(B).

FIGS. 8B(C) and 8B(D) were collected immediately after obtaining FIG. 8B(B); with the FAIMS "in operation", i.e. the DV was set to 3300 and the CV was changed to −5.0 V (FIG. 8B(C)) and −7.7 V (FIG. 8B(D)). These CV values were selected since they corresponded to the maximum values in the ion selective ("IS") CV spectra of the $16^+$ (CV=−5.0 V) and $8^+$ (CV=−7.7 V) charge states (also corresponding to the approximate peak maxima in the IS-CV-spectrum in FIG. 8B(A)). When the FAIMS was "turned off" in obtaining FIG. 8B(B), these charge of states of equine cytochrome c were still distinguishable. However, it is clear that the S/N is greatly improved for these charge states as shown in FIGS. 8B(C) and FIG. 8B(D) relative to those shown in FIG. 8B(B). The improvement of S/N for the $8^+$ charge state is greater than that for the $16^+$ because of a greater increase in the depth of the FAIMS trapping potential well (FAIMS focussing) of the $8^+$ charge state relative to that of the $16^+$ charge state. By setting the compensation voltage to the optimal value for any charge state in the IS-CV-spectrum, the S/N ratio for that individual charge state easily can be improved with the FAIMS is "in operation" relative to conditions in which the applied voltages are "turned off".

F) Other FAIMS Embodiments

Effective desolvation of the ESI ions is not limited to the geometry of the FAIMS devices described above. Recall the term FAIMS used herein globally refers to all the types of configurations of hardware which will have the capability of separating ions and/or focussing ions at atmospheric pressure using the high field ion mobility mechanism, and asymmetric waveform discussed earlier. From the point of view of the invention described in this disclosure, the effective 'desolvation' created by the FAIMS is the same for all of the geometries of FAIMS described here. The ion separation and/or ion focussing action of FAIMS only functions properly (or at all in the case of contaminated gases) when the gas stream in the FAIMS analyzer region, or FAIMS trapping region is substantially free of solvents and neutral contaminant molecules (as distinct from the normal components of the gas e.g. oxygen, nitrogen, argon, etc in purified air). This means that if the FAIMS has functioned as described in this disclosure, then it is assumed that the gases have been purified as required, and that the ions have passed through the FAIMS analyzer in a clean environment. This clean gas/ion mixture is exactly the prerequisite for introduction of ions into the mass spectrometer. If the FAIMS has functioned properly, the ions/gas mixture that leaves the FAIMS analyzer region is ideally suited for immediate introduction into the entrance (sampler) orifice of a mass spectrometer.

1) FAIMS-MS

As discussed earlier, one way to extend the functionality of FAIMS devices is to couple them together with a mass spectrometer. The use of a mass spectrometer together with a FAIMS device is advantageous because the mass spectrometer facilitates a mass-to-charge (m/z) analysis to determine the make-up of CV spectra more accurately. One possible FAIMS-MS embodiment is described here.

Figure 5A:
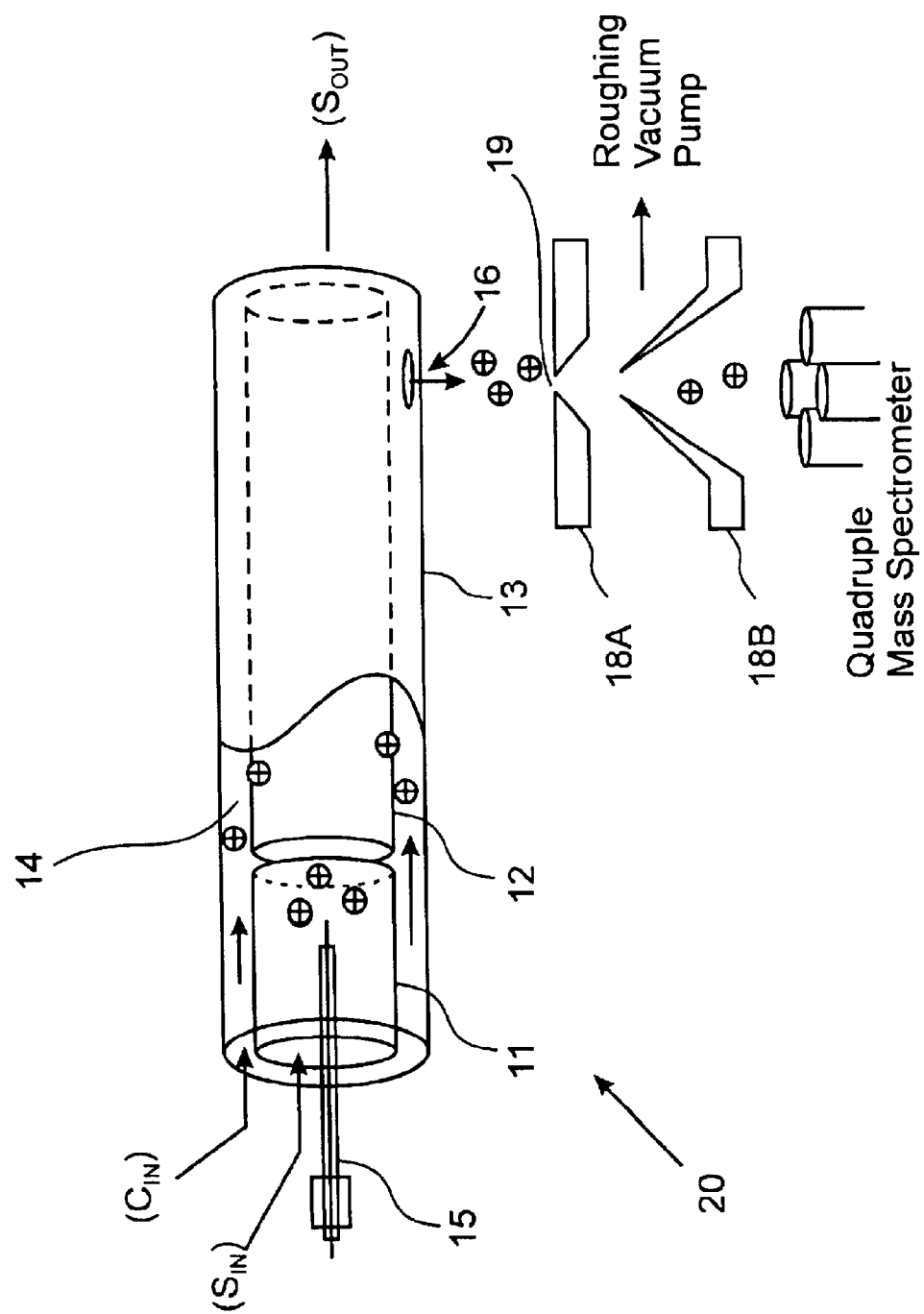
FIGS. 5A and 5B show schematically the coupling of the FAIMS apparatus of FIGS. 3A and 3B together with a mass spectrometer.
Figure 5B:
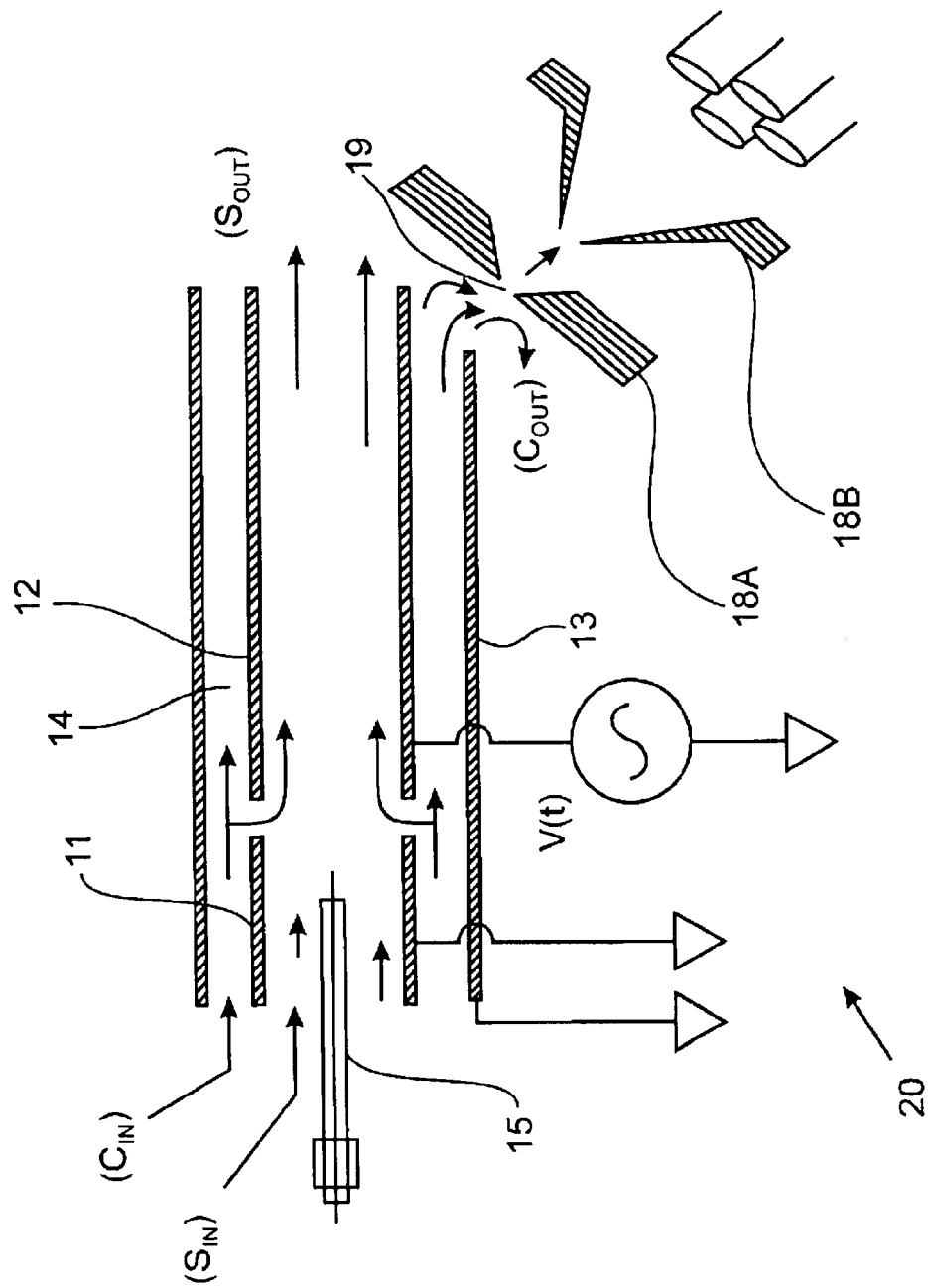

Refering to FIGS. 5A and 5B, the coupling of FAIMS and a mass spectrometer (FAIMS-MS 20) is shown schematically. The FAIMS-MS 20 of FIGS. 5A and 5B, and the Aft FAIMS-E 10 shown in FIGS. 3A and 3B, differ significantly only at the detection end of the instrument. In accordance with the invention, the electrometer 17 has been replaced by a sampler cone 18A, placed at the end of the FAIMS cylinders 12, 13 as is shown in a simplified form in FIG. 5B. The diameter of the orifice 19 in the sampler cone 18A is approximately 250 μm. The gas flows in the FAIMS-MS 20 are analogous to those in the FAIMS-E 10 except that the $C_{out}$ is divided into two components, namely the original $C_{out}$ and the flow through the orifice 19 into the mass spectrometer. The electrical waveforms applied to the long inner cylinder 12 are identical to those used in the FAIMS-E apparatus 10. The sampler cone 18A may be electrically insulated from the other components so a separate voltage OR can be applied to it. Furthermore, a voltage can be applied to the cylinders of the entire FAIMS unit ($V_{FAIMS}$) for the purpose of enhancing the sensitivity of the FAIMS-MS.

FIG. 5B shows the FAIMS cylinders 12, 13 at a 45 degree angle in relation to the sampler cone 18A of the mass spectrometer. FIG. 5A showed the FAIMS cylinders 12, 13 at a 90 degree angle in relation to the sampler cone 18A. The way (i.e., the angle between the two tubes of the FAIMS and the sampler cone 18A) in which the ions are extracted from the cylinders 12, 13 of the FAIMS-MS 20 into the mass spectrometer is not limited to these angles. Furthermore, the location in which the ions are extracted from the two tubes can also be changed. That is, the ions can be extracted anywhere along the separation region of the FAIMS.

2) Other Geometrical Considerations of the FAIMS-MS Interface

The FAIMS hardware described above represents only one example of the FAIMS device; the geometry of the separation region can be drastically changed. In this disclosure "FAIMS" has been used to describe the class of devices which have one of these two properties: (1) separation of ions at atmospheric pressure using the changes in ion mobility at high electric field (FIGS. 1) and (2) focussing or trapping of ions at atmospheric pressure by utilization of the changes in ion mobility at high electric field, and/or a combination of utilization of the changes in ion mobility at high electric field and at least one other force applied to the ions, including a gas flow, or an independently created electric field which acts to create a location in space wherein the ions cannot escape. The term focussing has been used to describe restriction of ions to a 2-dimensional, sheet-like space (free to move along the surface of the sheet) and ion trapping is used to describe the condition in which the ion cannot escape in any direction. Because of diffusion, and space charge repulsion of ions, the actual physical locations of the ions will generally be distributed over some space, rather than strictly located in one infinitely small physical location. This means that the 2-dimensional sheet described above has 'thickness'. This means that within the 3-dimensional trapping zone, which might be strictly speaking considered to be an infinitely small single point in space, the ions actually occupy a region that surrounds this single point, and the ions are in motion around the point. The ions will occupy a smaller physical space if the trapping potential well is deeper.

In practice, the two functions described above are accomplished by application of an asymmetric waveform in such a way that the ions are at 'low electric field' for a time period of the waveform, and at 'high electric field' for a shorter period of the waveform. This has been discussed in detail above. The other requirement, in addition to the asymmetric waveform, is a non-constant electric field. The first function described above i.e. ion separation can be achieved by use of a constant electric field between flat parallel plates as shown in FIG. 2. The ion focussing and ion trapping requires a non-constant electric field, normally occurring in a geometrical configuration in which the electrodes are curved, and/or are not parallel to each other. These non-constant electric fields can be created in a variety of ways. For example, a non-constant electric field may be created using electrodes which are cylinders or a part thereof; spheres or a part thereof; elliptical spheres or a part thereof; conical or apart thereof, and so on. Combinations of these shapes may also be used. Since the FAIMS technology is not well defined, some examples of FAIMS using other possible electrode geometries will be discussed.

Several ESI-FAIMS-MS spectra have been obtained by mounting the FAIMS-MS on a PE SCIEX Elan 5000 mass spectrometer (single quadrupole). The sampler orifice plate of the FAIMS-MS was threaded into the port typically used for the nickel "sampler cone" in an ICP/MS experiment on the Elan 5000. The interface of the Elan 5000 was modified to permit voltages to be applied to the sampler orifice cone (OR) and to the "skimmer cone". The SCIEX Elan 5000 instrument is typically used for elemental analysis by ICP/MS and is suited for high sensitivity detection of low mass (atomic) ions.

For ESI-FAIMS-MS experiments that required a wider mass range (e.g. proteins), an analogous interface was constructed for a PE SCIEX API 300 triple quadrupole mass spectrometer. As described above, a voltage was applied to the sampler cone 18A, but the skimmer cone 18B of the API 300 instrument permitted tandem mass spectrometry (MS/MS) experiments to identify ions whose structures might be otherwise very difficult to establish. Single ion monitoring experiments during which the compensation voltage applied to the FAIMS was scanned produced "ion selected CV spectra" (IS-CV spectra). Scanned MS experiments displayed as the sum of intensity of all detected ions are called "total ion current CV spectra" (TIC-CV spectra). These spectra can be compared to CV spectra collected with the electrometer-based instrument. The mass spectrum collected at a fixed value of CV revealed the identity of any ions transmitted through the FAIMS under fixed conditions of DV and CV.

Quadrupole mass analyzers were used simply because of their availability in our laboratory. Note that other types of mass analyzers (e.g., ion trap, time-of-flight, fourier transform ion cyclotron resonance, etc.) and hybrids thereof could also be used with the ESI-FAIMS-MS interface. The FAIMS was placed at a 45 degree angle and also at a 90 degree angle relative to the mass analyzers for various experiments described in this disclosure. However, other angles can also be used.

3) FAIMS-R2-Prototype

Figure 9A:
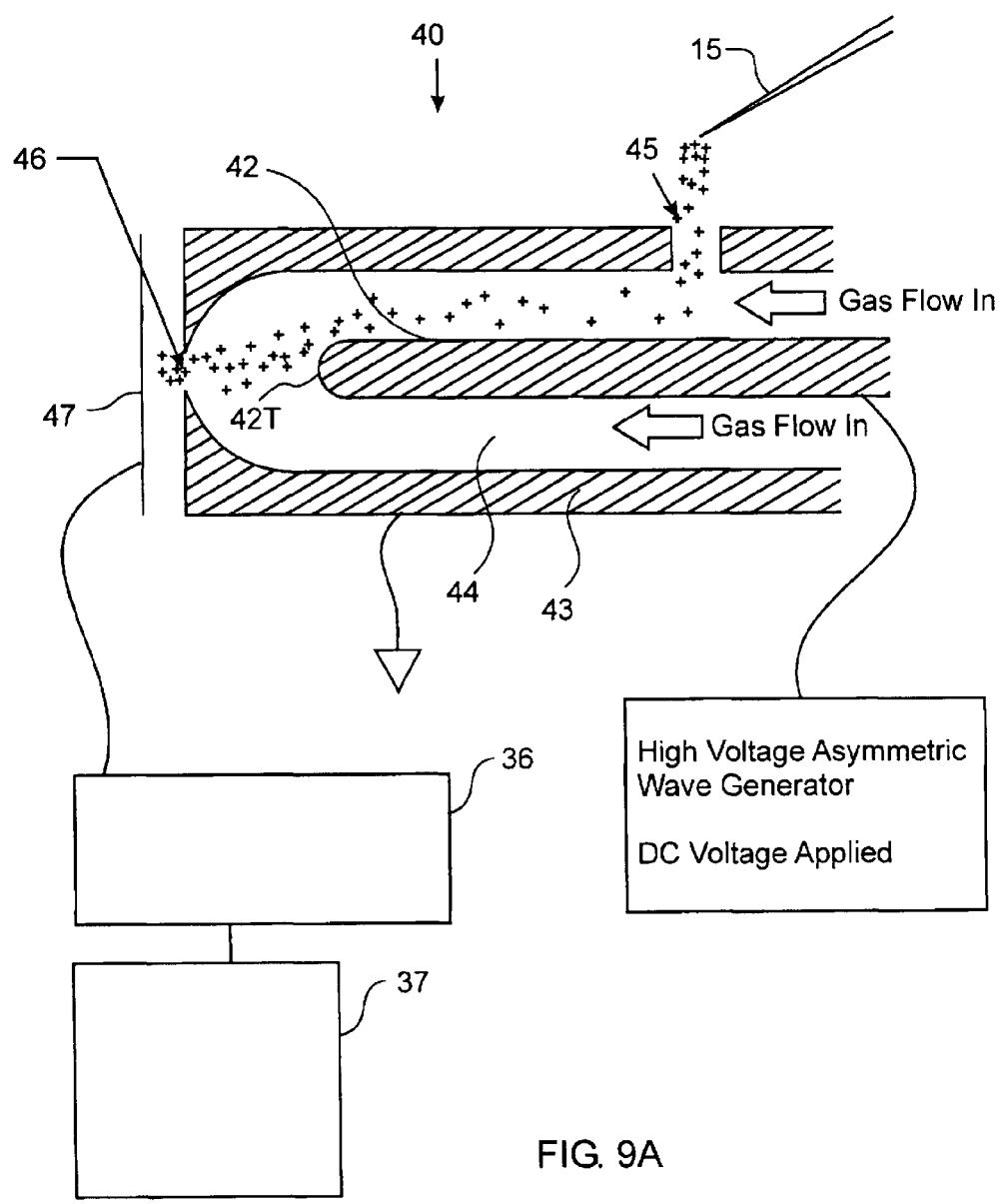
FIGS. 9A and 9B show schematically a first embodiment of a 3-dimensional atmospheric pressure high field asymmetric waveform ion trap, referred to as the FAIMS-R2-prototype.
Figure 9B:
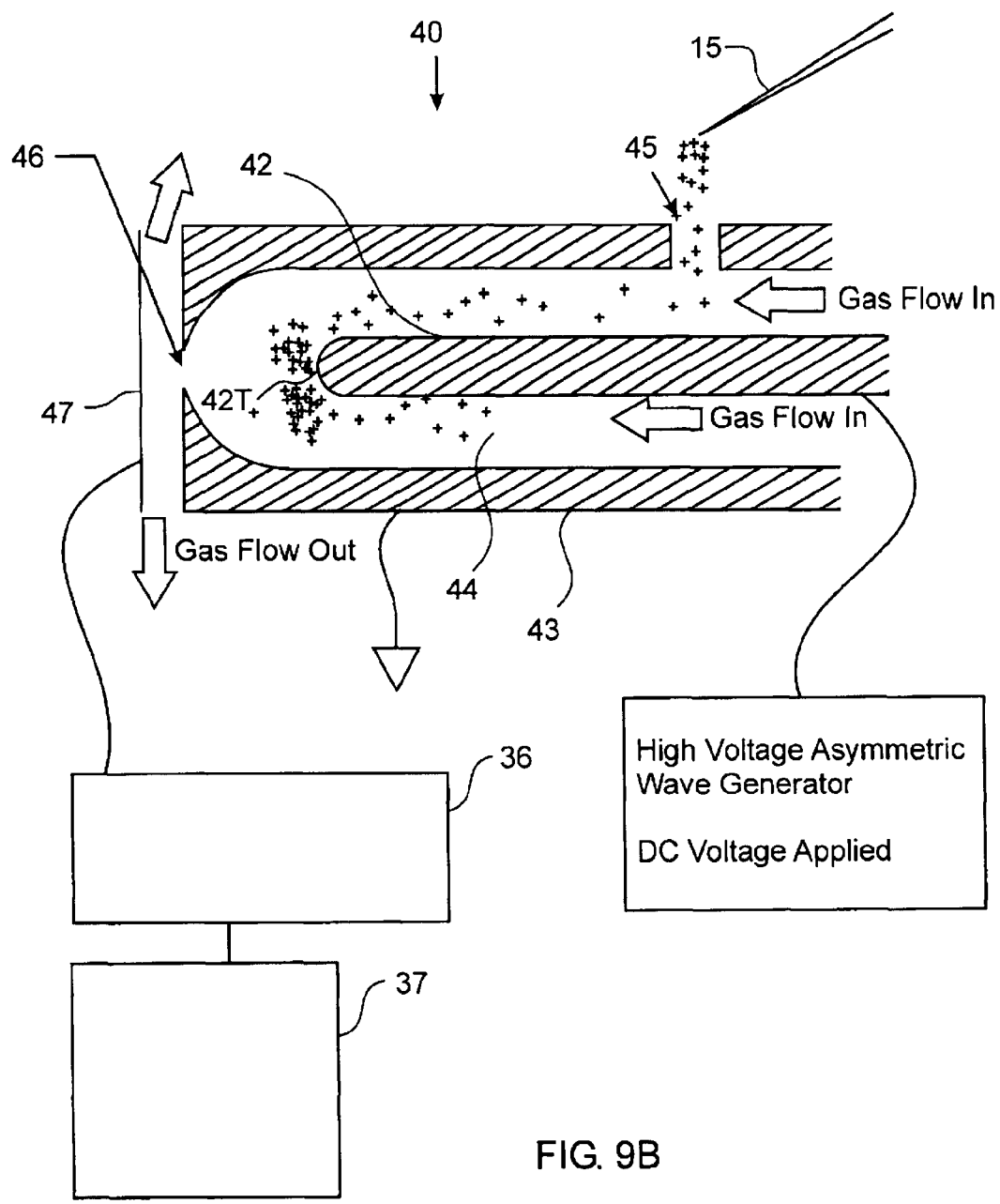

Referring to FIGS. 9A and 9B, the device which will be referred to as the FAIMS-R2-prototype 40 is shown. Here, the asymmetric waveform V(t) and the compensation voltage CV are applied to the inner, solid, electrode 42, having a diameter of about 2 mm. The outer, electrically grounded electrode 43 has an inner diameter of about 6 mm, thereby allowing an annular space of about 2 mm between the electrodes. This annular space has been referred to as the FAIMS analyzer or FAIMS analyzer region 14, 34, 44 in the discussion above, and for simplicity we will continue to use this terminology. The ions are created by ionspray in a closed cell (not shown) located adjacent to a 0.5 mm hole through the wall of the outer cylinder. As shown in FIG. 9A, ions are driven by the high electric field generated by the ionization needle 15 (held at about +1500 to 2000 V), through the 0.5 mm hole 45 (the ion inlet), and into the FAIMS analyzer region 44 (only those ions travelling directly toward the hole 45 are shown for simplicity). Inside the FAIMS analyzer region 44, near this hole 45, the electric fields and the gas flow (shown to be flowing from right to left in FIGS. 9A and 9B) are perpendicular to each other and the ions experience the 2-dimensional focussing effect described in the earlier sections above. However the inner electrode 42 in the device shown in FIG. 9A, terminates about 2 to 4 mm from the end of the outer electrode 43. The inner surface of the outer electrode 43 at the downstream end is contoured in such a way as to maintain approximately the same electric fields (i.e. created by the application of DV and CV) as would be experienced along the length of the FAIMS analyzer region 44. The end of the outer electrode has an exit grid 46 (the ion outlet) comprising a hole (about 2 mm) which is covered with a fine, high transmission metallic screen. The gas flowing through the device 40 also flows freely through the grid 46 and exits from the space between the outer electrode 43 and a collector plate 47. In the absence of any applied voltages (i.e. DV and CV) the ions will travel through the device very much as shown in FIG. 9A. The ions enter the analyzer region 44, flow with the gas out through the exit grid 46 of the outer electrode 43, and the few remaining ions are attracted to an ion collector plate 47 biased at about −5 V. The collector plate 47 was connected to a high gain current amplifier electrometer 36 (e.g. Keithly 428) and an oscilloscope 37.

The application of an asymmetric waveform of the type shown in FIG. 7 resulted in the ion focussing behaviour described above except that the focussing action extended around the generally spherically shaped terminus 42T of the inner electrode 42, as shown in FIG. 9B. This means that the ions cannot escape from the region around the terminus 42T of the inner electrode 42. This will only occur if the voltages applied to the inner electrode 42 are the appropriate combination of CV and DV as described in the discussion above relating to 2-dimensional focussing. If the CV and DV are suitable for the focussing of an ion in the FAIMS analyzer region 44, and the physical geometry of the inner surface of the outer electrode 43 and the curved terminus 42T in FIGS. 9A and 9B does not disturb this balance, the ions will collect near the terminus 42T as shown in FIG. 9B. Several contradictory forces are acting on the ions in this region near the terminus 42T of the inner electrode 42. The ion cloud shown near the terminus 42T of the inner electrode 42 in FIG. 9B would like to travel from right to left to the exit grid 46 in the manner shown in FIG. 9A, because of the force of the gas flow. This also means that the ions cannot migrate back from left to right, toward the ion source 15. The ions that get too close to the inner electrode 42 are pushed back away from the electrode 42, and those near the outer electrode 43 will migrate back towards the inner electrode 42, because of the application of the negatively polarized CV. The ions are captured in every direction, either by forces of the flowing gas, or by the electric fields (electric potential well) of the FAIMS mechanism.

Note that, while the above discussion refers to the ions as being "captured", in fact, the ions (and neutrals) are subject to 'diffusion'. Diffusion always acts contrary to focussing and trapping. The ions will always require an electrical, or gas flow force to reverse the process of diffusion. This means that although the ions may be focussed into an imaginary cylindrical zone in space (with almost zero thickness), or within a 3-dimensional ion trap, in reality it is well known that the ions will actually be dispersed in the vicinity of this idealized zone in space because of diffusion. This means that ions will always be "distributed" over some region, rather than all precisely located in the same place. This is important, and should be recognized as a global feature superimposed upon all of the ion motions discussed in this disclosure. This means that, for example, a 3-dimensional ion trap will actually have real spacial width, and leak for several physical, and chemical reasons.

Expanding on the chemical effects in FAIMS, if an ion collides with a neutral molecule and temporarily forms a stable complex, this complex may drift out of the FAIMS focussing or trapping region because this new complex has high field mobility properties which are different from the original ion. This means that the complex may have behaviour at high electric field (see FIG. 1) which differs from the original simple parent ion. For example (at the extreme) the original ion may be of type A, and the new complex of the type C shown in FIG. 1. If this is the case, the new complex will not be trapped at the prevailing DV and CV conditions. The collision of any of these ions with the walls of the device will soon result in loss of the ions from the trap. Although the original ion itself may continue to be trapped, the removal of this ion via "chemical" effects is entirely possible, and is the reason the FAIMS analyzer will fail in the presence of significant water vapour or contaminants in the gas flows. The FAIMS analyzer works best in very clean conditions. During operation in P2 mode, the requirement for a high purity gas is somewhat relaxed.

Figure 10:
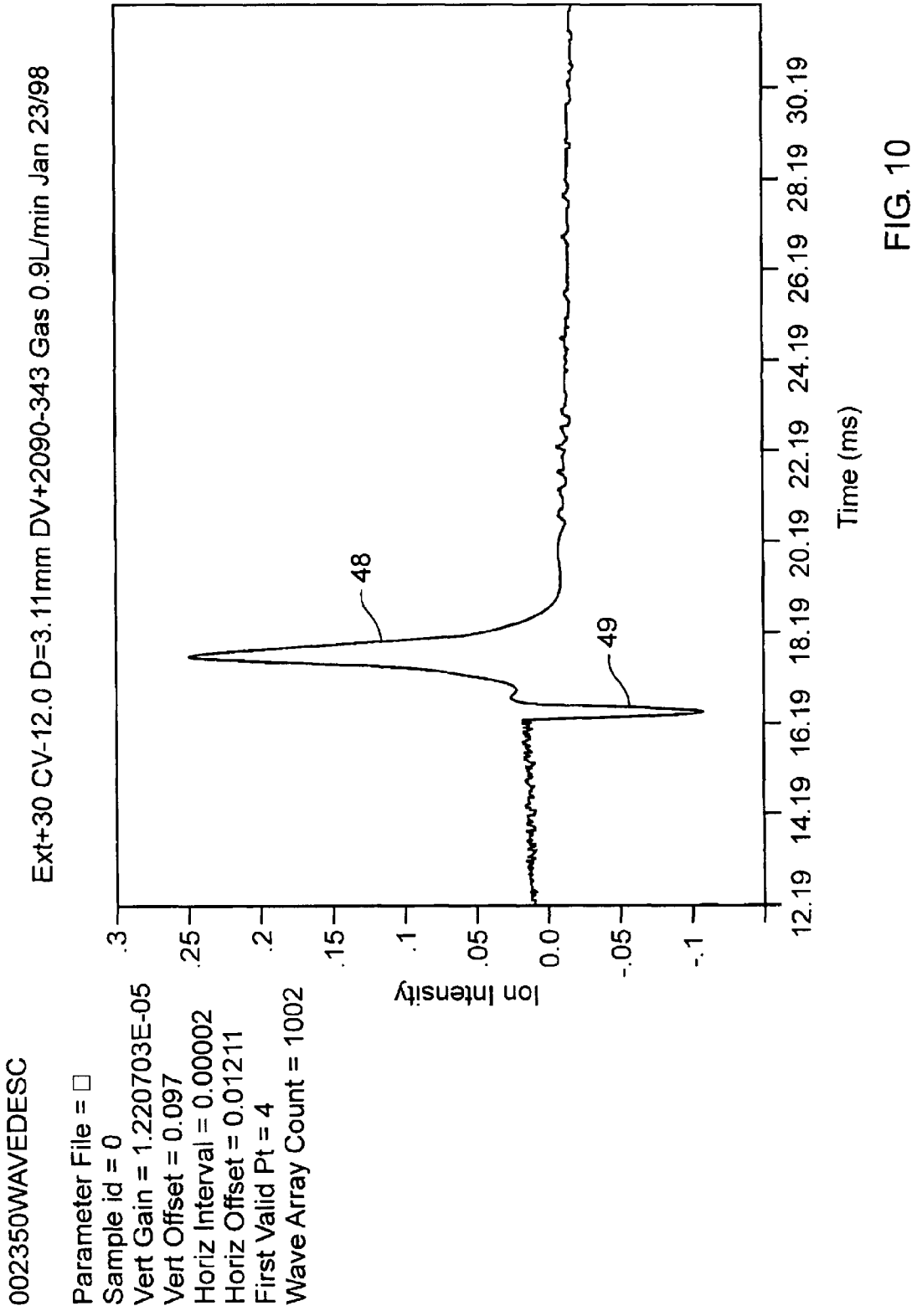
FIG. 10 shows the experimental result for extraction of ions trapped using the FAIMS apparatus of FIG. 9A with the extraction voltage set at +30 volts.

FIG. 10 is an example of experimental results with the FAIMS-R2-prototype, The dimensions of the electrodes were described above, for FIGS. 9A and 9B. DV was 2090 volts, CV −12 volts, and the gas flow through the device was 0.9 L/min. The DV and CV were applied for about 16 msec, and these voltages replaced by an extraction voltage. The trace in FIG. 10 represents results for the ions extracted wit a voltage of +30 volts. The extraction of trapped ions results in a positive pulse recorded in the Figure. The negative pulse is the transient that occurs when the DV and CV voltage are removed and replaced by the extraction voltage. It is clear from the data shown in FIG. 10 that the application of a extraction voltage will yield a short, intense ion signal. This occurs since the ions which were trapped at the tip of the inner electrode were pulsed out of the trap by the +30 volts. The negative-going pulse shown in FIG. 10 appears even without ion introduction, but the positive-going ion signal is absent if the ion production device (e.g. ionspry source in FIG. 12) is absent, or the device is turned off.

Although the diagram of FAIMS-R2-prototype in FIGS. 9A and 9B, illustrates an ion collection plate 47, in accordance with the present invention, the ion collector plate can be replaced with the sampling cone 18A of a mass spectrometer. As noted above for the other types of FAIMS, the ion/gas stream from FAIMS-R2-prototype is ideally suited for immediate introduction into a mass spectrometer because the ions have been substantially desolvated, and the gas stream is largely free of contaminants and solvent vapours.

4) FAIMS-R3-Prototype

Figure 11A:
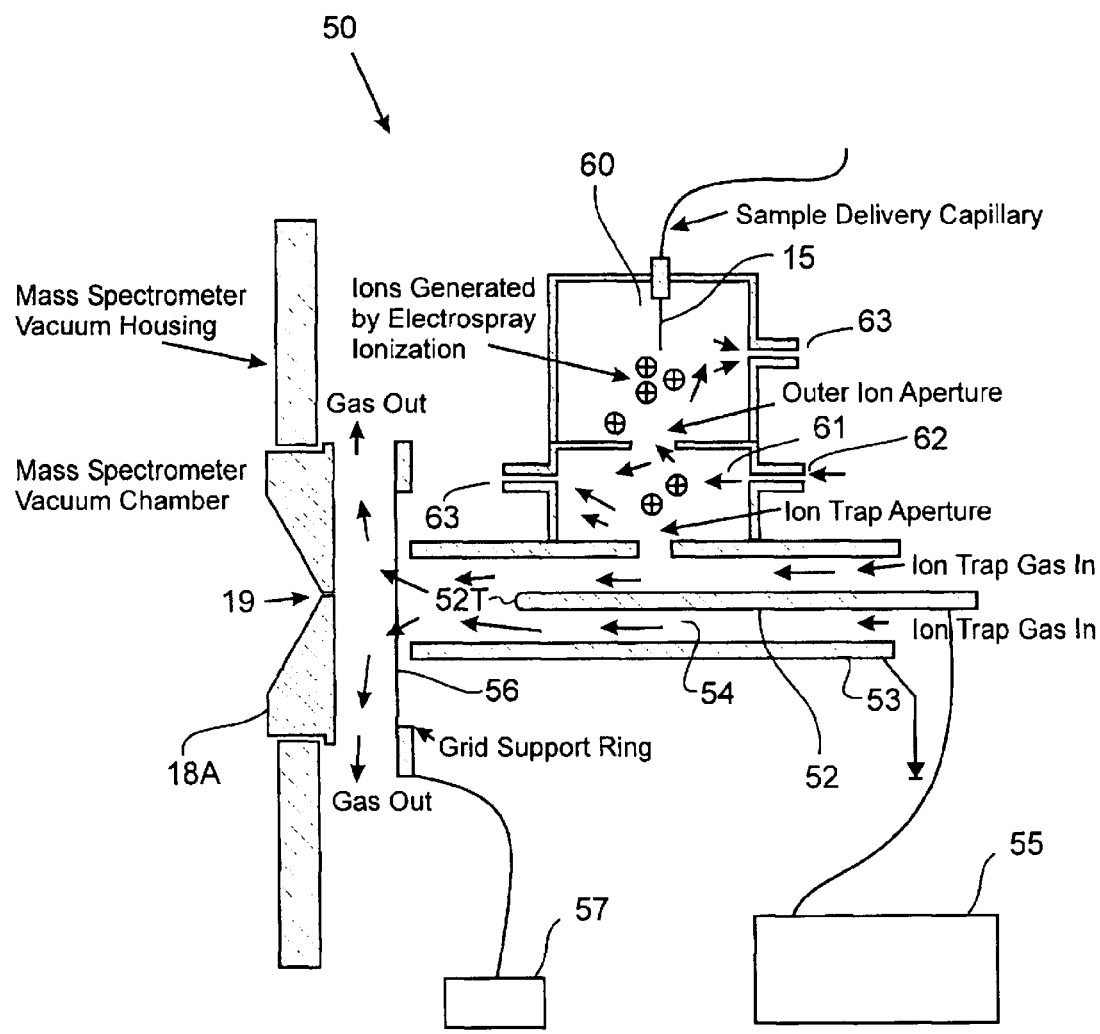
FIGS. 11A–11C show a second embodiment of a 3-dimensional atmospheric pressure high field asymmetric waveform ion trap, referred to as the FAIMS-R3-prototype.
Figure 11B:
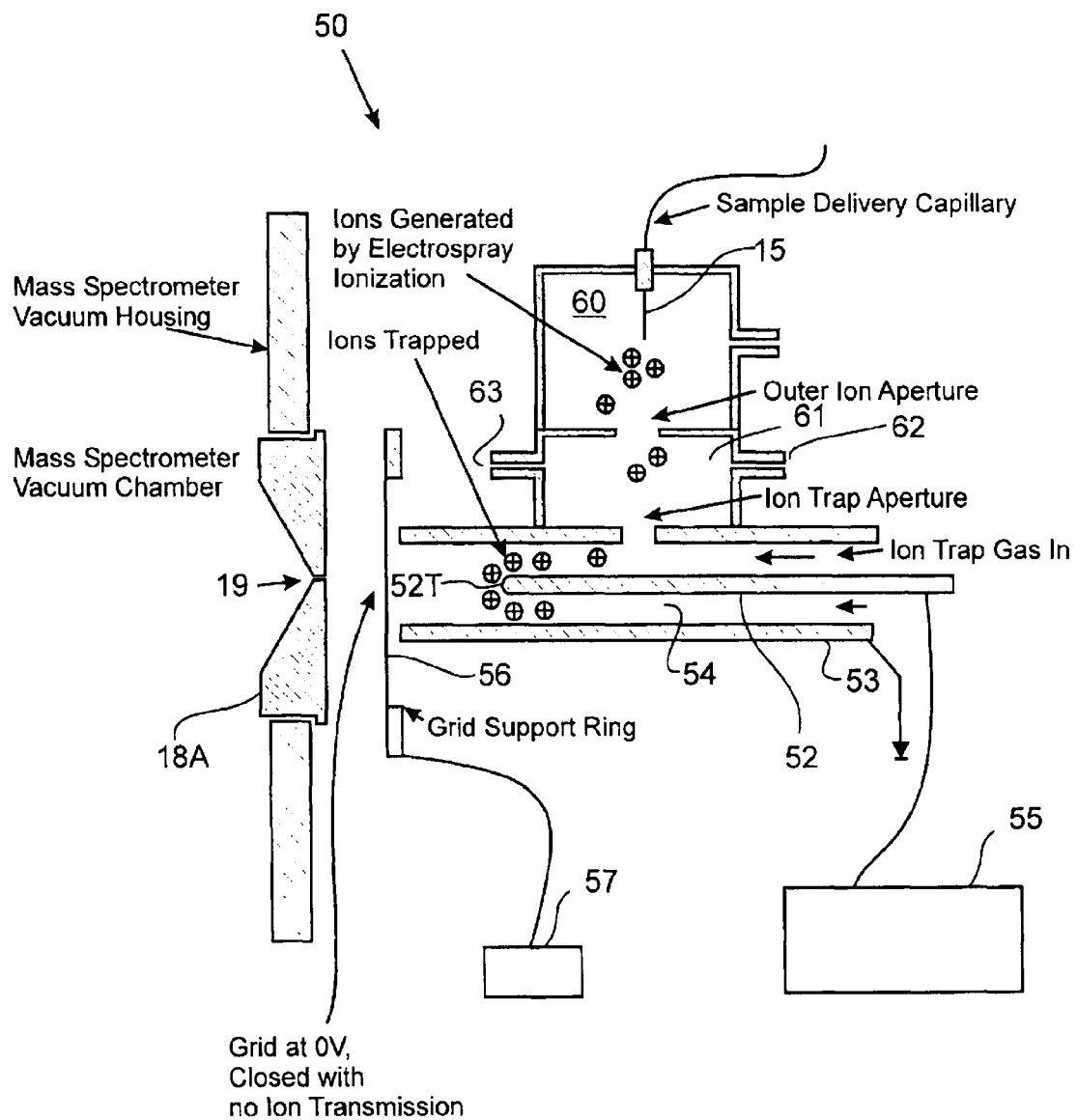
Figure 11C:
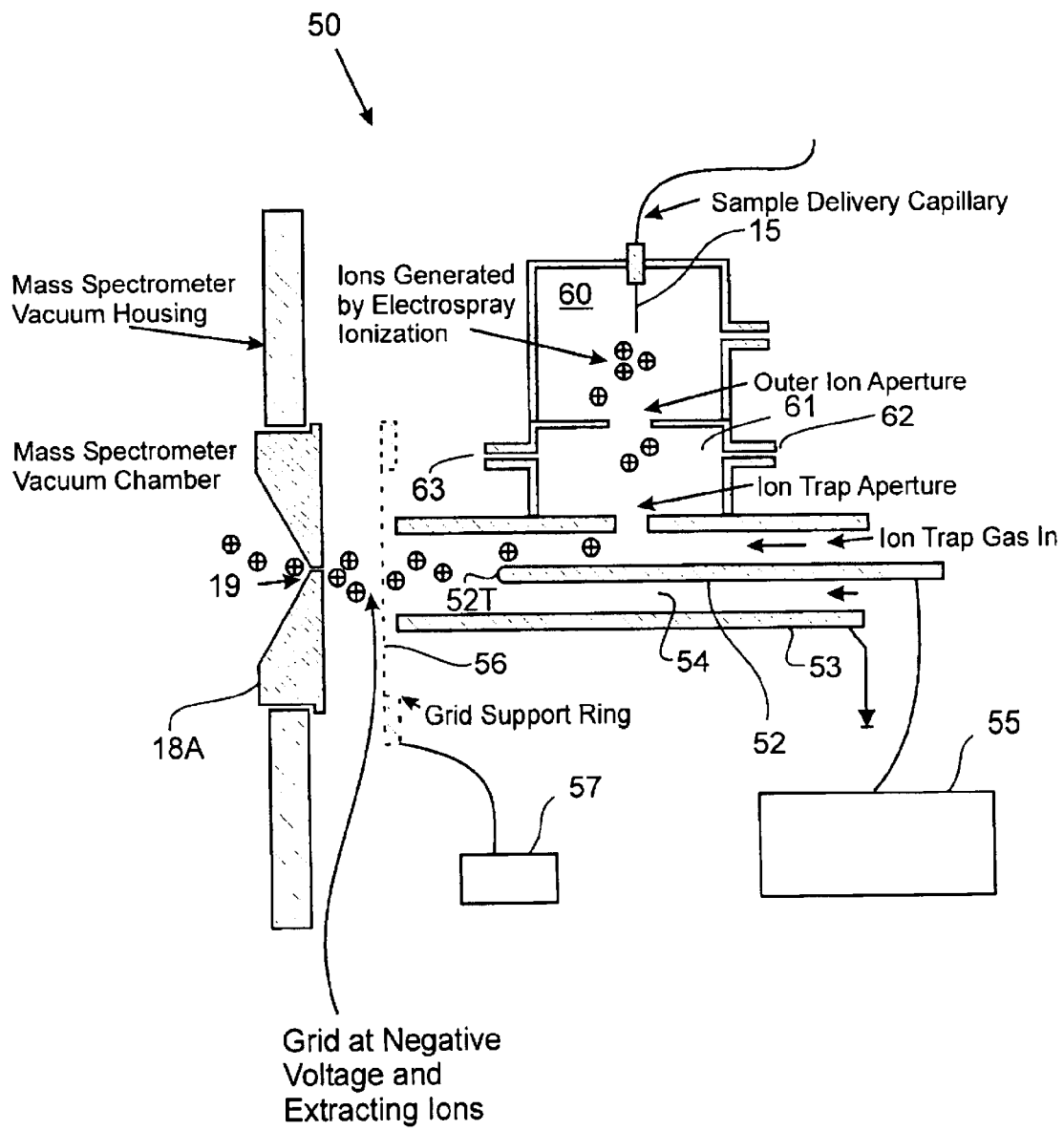

Now referring to FIGS. 11A through 11C, the FAIMS-R3-prototype 50 is shown. This device is configured for detection by mass spectrometry, and a sampler cone 18A, through which gas and ions are pulled into the vacuum chamber of a mass spectrometer is shown on the left side of FIGS. 11A–11C. The right side of the vacuum housing, and sampling cone 18A, is at atmospheric pressure. The left side of those components is labelled "Mass Spectrometric Vacuum Housing", and is typically below 1 torr pressure. In most systems a second orifice (not shown) leads the actual mass analyzer region of the mass spectrometer which is usually below 10 torr pressure.

Figure 11D:
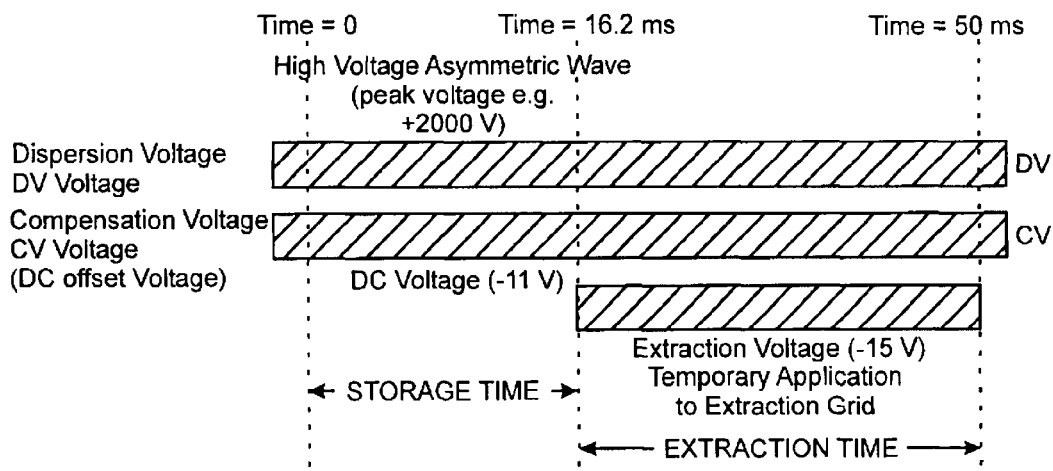
FIG. 11D shows a timing diagram for a voltage applied to the FAIMS apparatus of FIGS. 11A–11C.
Figure 11D:
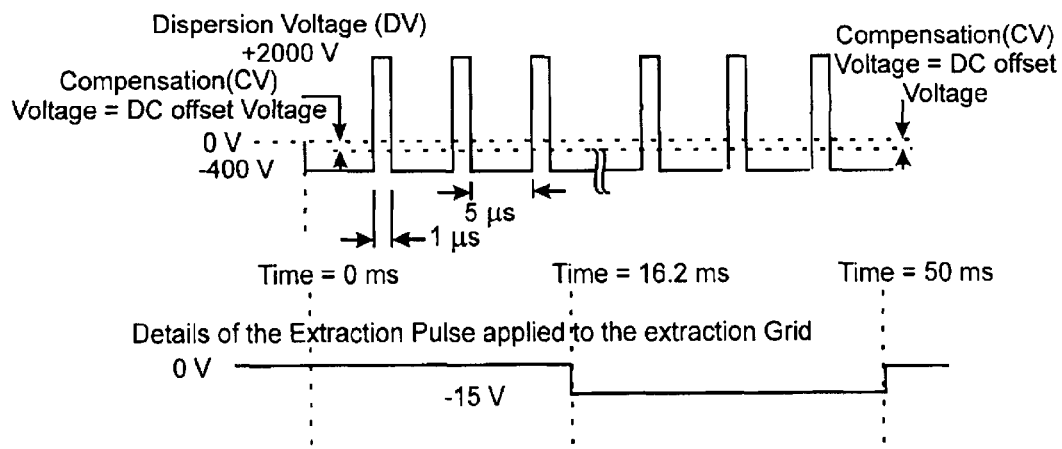

The FAIMS-R3-prototype analyzer 50 shown in FIG. 11A consists of an inner, solid, cylindrical electrode 52 of about 2 mm diameter, and an outer electrode 53 which is about 6 mm inner diameter. The center electrode 52 is powered, through an electrical connection, by an RF asymmetric waveform generator power supply 55. Both DV and CV are supplied by this generator 55. The waveforms, and the timing diagram are shown in FIG. 11D. As shown in FIG. 11D, the asymmetric waveform is applied continuously to the inner electrode 52. No other variation of the voltage (other than manual selection of various CV and DV settings) is applied to the inner electrode 52.

Referring back to FIG. 11A, gas enters the FAIMS-R3-prototype 50 from the right side and flows along the annular space comprising the FAIMS analyzer region 54, and out through the open end of the outer electrode 53. Adjacent to the open end (left side) of the outer cylinder 53 is an exit grid 56 comprising a fine, thin-wired metallic grid which is electrically isolated from the outer electrode 53, and has an electrical connection to a grid electric pulse generator power supply 57. The voltage on the grid 56 can be changed stepwise using this power supply. The grid voltage and timing diagram is shown in FIG. 11D. The grid is typically maintained between −5 and +5 V during the ion storage time shown in FIG. 11D. The grid will then be stepped (100 ns transition) to between −5 V and −50 V in order to extract the ions from the 3-dimensional atmospheric pressure trap which is located in front of the spherical terminus of the inner electrode 52T. FIG. 11B shows schematically the approximate location of the ions during the storage period. It should be kept in mind that the ions trapped here must have the correct high field ion mobility (see FIG. 1) so that their "net" motion is zero at the combination of CV and DV being applied to the storage device (the term "net" is used because the ion is constantly moving back-and-forth due to the application of the asymmetric waveform: if the ion returns to the same location repeatedly, then the "net" motion caused by the application of DV and CV is zero). For example, the ions of type $(H_2O)_nH^+$ will be stored in the geometry shown in FIG. 11A–11C at a DV of about +2000 V and a CV of approximately −10 V (typical of P1 mode). At conditions very different (e.g. at DV 2500 and CV −5 V) from this combination of DV and CV the $(H_2O)_nH^+$ ions will not assemble into one physical location as shown in FIG. 11B. Instead, these ions will collide with the walls in the FAIMS analyzer region 54. At a second set of DV and CV conditions, such as the DV 2500 and CV −5 V noted above, another ion (e.g.(Leucine)$H^+$) may be able to collect at the tip 52T of the inner electrode 52 as shown in FIG. 11B.

As explained earlier, near the terminus 52T of the inner electrode 52 shown in FIG. 11B, the ions are restricted in motion because of several contrary forces. The gas flowing along the FAIMS analyzer region 54 applies a force which will prevent migration of ions from the left to right (FIG. 11B) back toward the ion source, and this force will also tend to pull the ions out of the trap towards the exit grid shown at the left end of the outer electrode. The electrical forces characteristic of FAIMS maintain the ions at a fixed distance from the sides of the inner electrode 52: (1) the ions which are too distant from the inner electrode 52 are attracted to the inner electrode 52 because of the negative polarity of the applied dc offset, i.e. a negative CV; and (2) the ions close to the inner electrode 52 are pushed away because of the increase of the ion mobility at high field (see FIG. 1) assuming the ions are of type A.

FIG. 11C illustrates the removal of ions from the 3-dimensional atmospheric pressure trap via a stepwise change to the voltage applied to the grid electrode 56. If the voltage applied to the grid 56 is decreased from, say, 0 V to −15 V as shown in the timing diagram FIG. 11D, the ion trap is reduced or eliminated, and the ions are free to escape under the influence of the gas flow, or by the electric field which might pull the ions toward the exit grid 56.

The FAIMS-R3-prototype 50 shown in FIGS. 11A–11C is appropriate for detection of ions produced by electrospray ionization (ESI). FAIMS is highly sensitive to moisture and contaminants in the gas entering the analyzer region. It is usual that contaminants, or too much water vapour, will result in complete loss of signal, and failure of the FAIMS to function in the manner described in this disclosure. Since electrospray ionization involves the high-voltage-assisted-atomization of a solvent mixture, the amount of water and other volatile solvents is far too high to be tolerated in the FAIMS. This will mean that the ESI-FAIMS combination will always require a type of gas-isolation, curtain gas, or counter-current gas flow, to prevent neutral solvent molecules from entering the FAIMS analyzer. One method to accomplish this is shown in FIGS. 11A–11C. The FAIMS is separated from the ESI chamber 60 by a small chamber 61 which has provision for gas inlets 62 and gas outlets 63. If a flow of gas enters this intermediate chamber 61, and a portion of the gas flows toward the ESI chamber, then the neutral solvent molecules will exit via the port on the ESI chamber, and will be prevented from entering the vicinity of the entrance to the FAIMS. The electrospray needle 15, shown in FIGS. 11A–11C is more likely to be in a horizontal plane or lower than the FAIMS analyzer region 54, rather than the higher, vertical position shown. This minimizes the tendency for very large droplets to fall via gravity, into the FAIMS analyzer region 54. In a horizontal or lower configuration the large droplets will fall into the bottom of the ESI chamber 60, which could (optionally) have a drain for removal of excess solvent.

Figure 12:
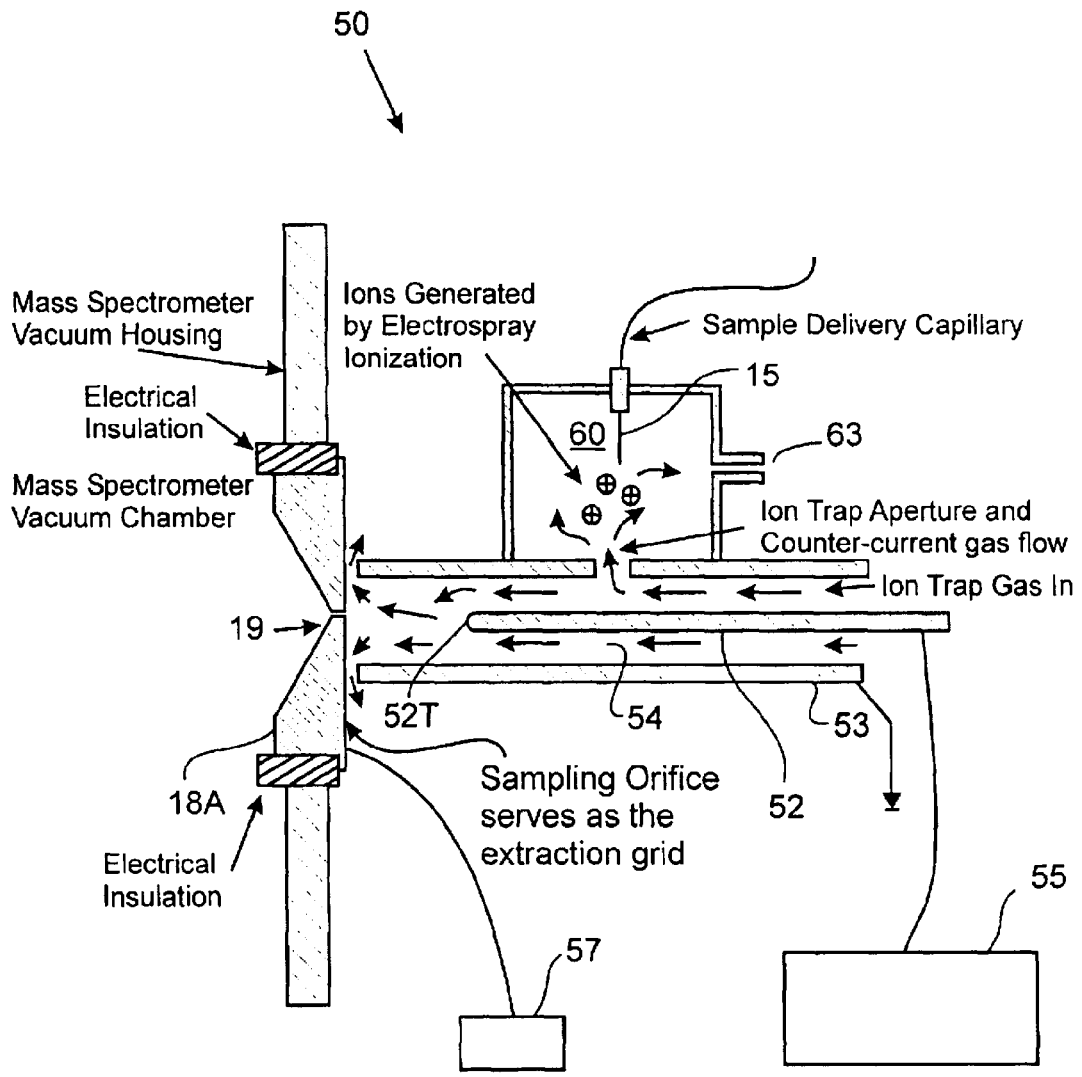
FIG. 12 shows an alternative embodiment of the FAIMS apparatus of FIGS. 11A–11C, having a simplified electrospray ionization chamber, and using the sampler cone as an extraction grid.

The counter-current of gas can be achieved in a second way shown in FIG. 12 (gas flows are emphasized, and most of the ions are omitted). If the FAIMS analyzer gas flow is adjusted so that some of the gas will exit the FAIMS analyzer region 54 into the ESI chamber 60, the entrance of neutral contaminants can be avoided. This may result in higher ion transmission than that for the device shown in FIGS. 11A–11C, but the device may not be user-friendly since accidental gas flow adjustment such that the gas from the ESI chamber 60 is passed into the FAIMS analyzer region 54 may compromise FAIMS performance for some period of time (hours) after the accident. Note also that the exit grid electrode 56 FIGS. 11A–11C) has not been shown in FIG. 12. In this embodiment the 'extraction' pulse that destroys the ion trap is applied to the mass spectrometer sampling cone 18A.

5) FAIMS-R4-prototype

Figure 13A:
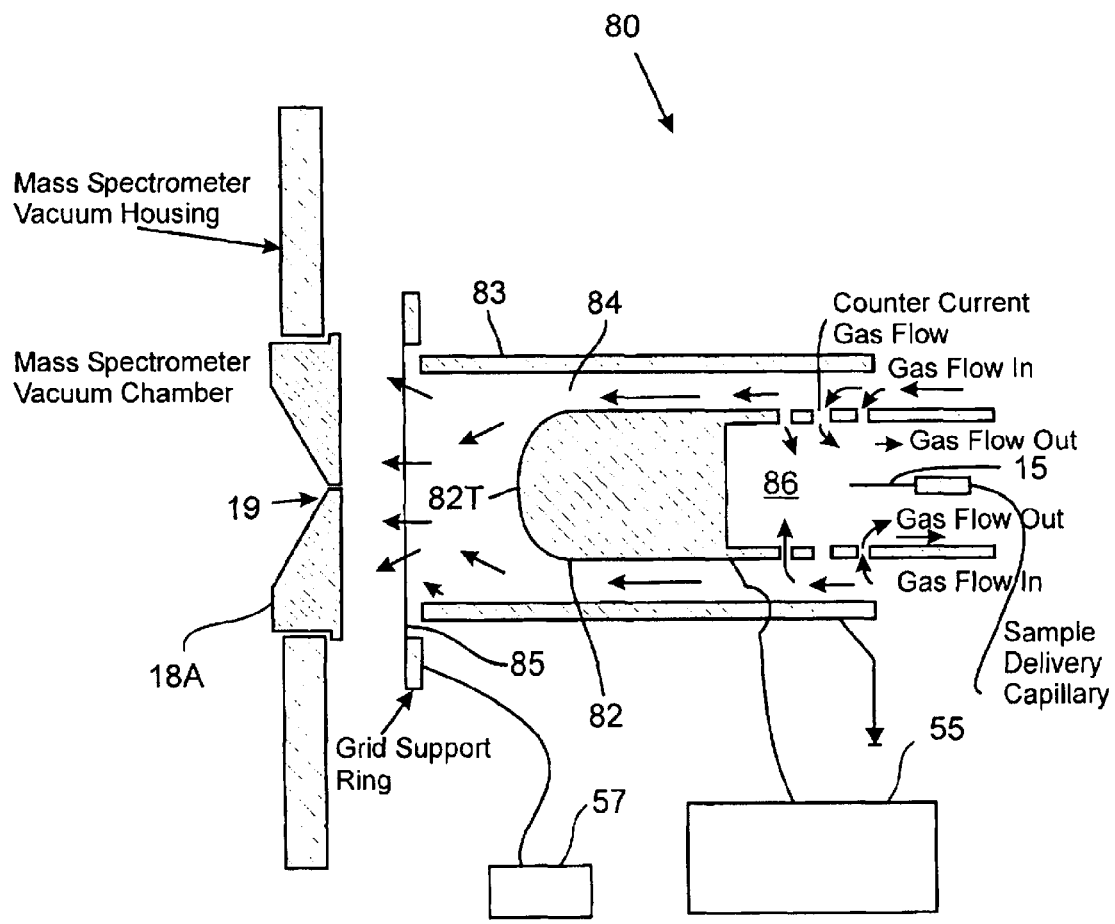
FIGS. 13A–13C show schematically an alternative embodiment of a 3-dimensional atmospheric pressure high field asymmetric waveform ion trap.
Figure 13B:
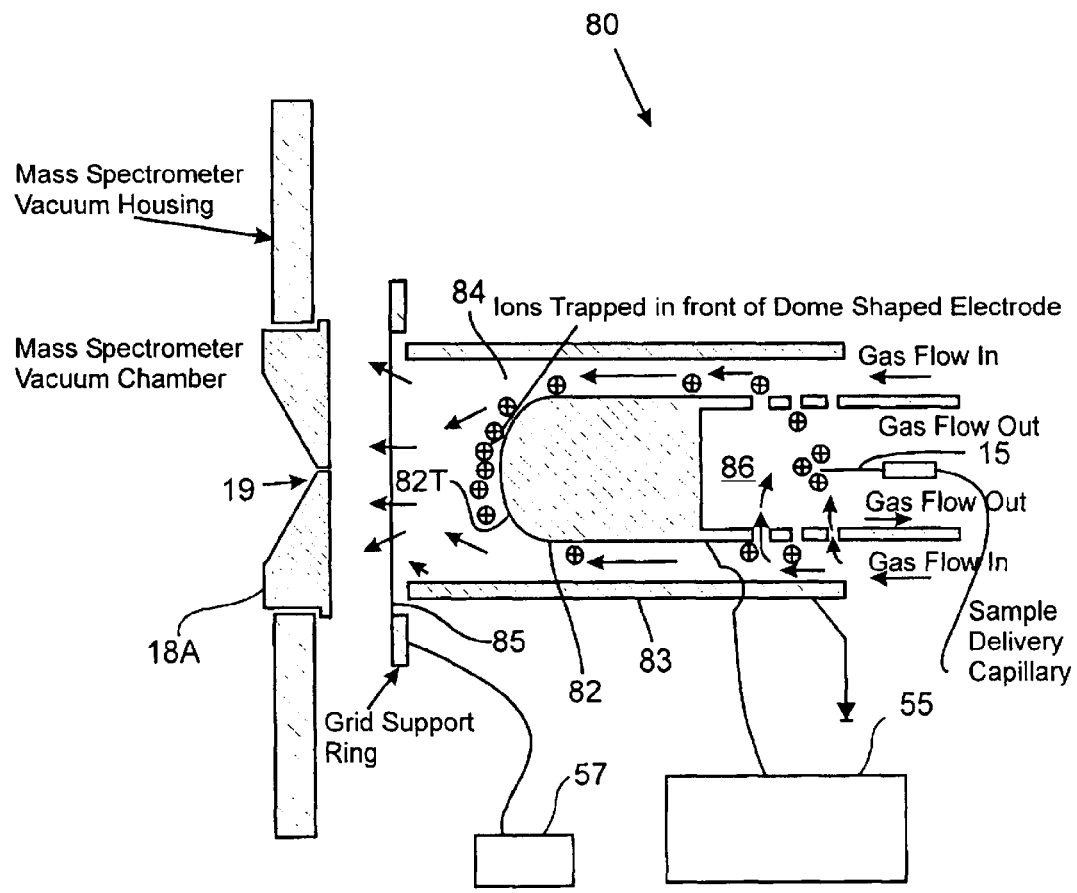
Figure 13C:
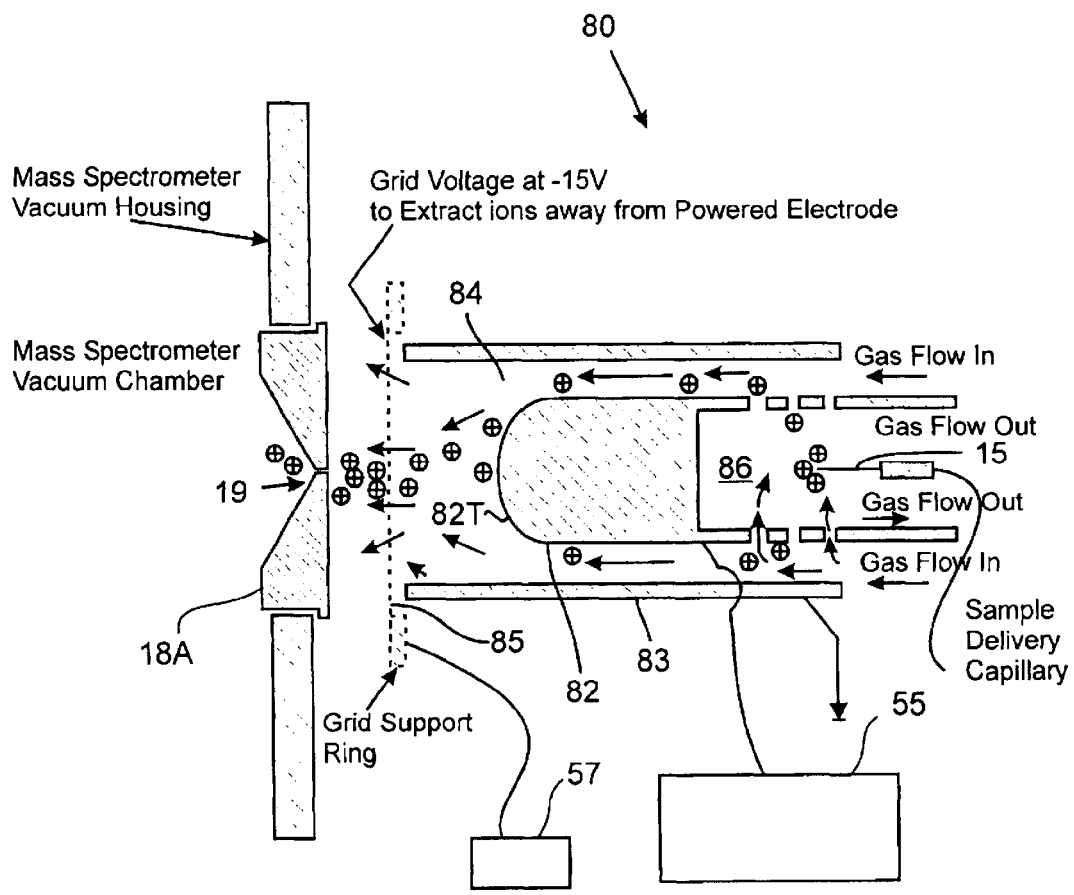

Now referring to an alternative embodiment shown in FIGS. 13A–13C, referred to as FAIMS-R4-prototype 80, a FAIMS 3-dimensional atmospheric pressure ion tap is shown in which the electrospray (or other ionization) occurs within the radius of the inner electrode 82. In general, ions may be introduced to the FAIMS analyzer region 84 either from outside (external) to the outer electrode 83, or from inside (internal) the inner electrode 82. The latter is less convenient because the dimensions are small, and the radius of the inner electrode 82 must be much larger than can be used in devices using the external ion source. Moreover, the ionization source (e.g. ESI needle) may be susceptible to the influence of the high voltages applied in the asymmetric waveform. The electrode immediately surrounding the ionization source is electrically grounded in the FAIMS shown schematically in FIG. 3A and 3B.

In the device shown in FIGS. 13A–13C, the inner electrode 82 would be about 14 mm outer diameter, and the outer electrode 83 about 18 mm inner diameter, with about 2 mm annular space (FAIMS analyzer region 84) between these two concentric cylinders 82, 83. The end of the irercylinder 82T (left end in FIGS. 13A–13C) is closed, and shaped either spherically, or cone shaped as appropriate to maintain the electric fields suitable for FAIMS ion trapping in all locations near the end of the electrode 82T. The inside of the outer cylinder electrode is shown to be uniform in diameter in FIGS. 13A–13C, but with wide diameter inner electrodes 82 such as shown in FIGS. 13A–13C, it is very likely that the FAIMS analysis conditions will be better maintained if the inner surface of the outer electrode is contoured very much like that shown in FIGS. 9A and 9B. This will maintain substantially constant distance between the inner electrode, and the outer electrode near the spherically shaped (or conical etc.), closed end 82T of the inner electrode 82.

Gas flows enter the end of the FAIMS analyzer region 84 shown in FIGS. 13A–13C (right hand side of the FAIMS in the figure), and flow toward the closed end or terminus 82T of the inner electrode 82. Beyond the terminus 82T of the inner electrode 82 the gas flow passes through an exit grid 85 comprising a high transparency, fine-wire grid, and exits through the space between the mass spectrometer sampler cone 18A and the exit grid 85. A portion of the gas flows into the sampler cone orifice 18A, drawn by the vacuum of the mass spectrometer. Some of the ions which have passed through the exit grid 85 during the extraction time period will also be drawn into the mass spectrometer, by gas flows and by electrical fields.

Some of the gas entering the FAIMS analyzer region 84 shown in FIGS. 13A–13C must be permitted to flow inwards (i.e. the counter current gas flow) from The analyzer region 84 into the ionization region 86, thereby preventing neutral molecules, large liquid droplets and other unwanted non-charged components from passing into the FAIMS analyzer region 84. These components would contaminate the gas in the analyzer 84, and the ion focussing and trapping described elsewhere in this disclosure will be degraded. The device therefore may fail if the gas flow from the FAIMS analyzer into the ionization region is reversed during electrospray experiments. If the ionization occurs in a very clean non-contaminated gas, then this restriction on the gas flow direction may be relaxed (e.g. ionization of clean gas with radioactive $^{63}$Ni foil, corona discharge ionization, ionization by UV light radiation etc.). During operation in P2 mode the requirement for high purity gas is somewhat relaxed.

The device shown in FIGS. 13A–13C operates in a manner analogous to that described previously. The tons pass radially out of the ionization region 86, transported by electric fields against the radially inward flowing gas. Having passed into the FAIMS analyzer region 84 the electric fields will either confine the ion inside the analyzer region 84 (focussing or trapping), or the ion will collide with the walls of the device because of application of DV and CV which are not appropriate. Assuming that the DV and CV are appropriate for one of the ions in the sample, that ion will be focussed in the FAIMS analyzer region, and flow with the gas (since in the analyzer region the gas and electric fields act perpendicularly to each other) toward the closed, dome-shaped terminus 82T of the inner electrode 82. If the trapping fields (electrical potential well) remain appropriate, the ions will assemble near the terminus 82T of the inner electrode 82 as shown in FIG. 13B. This will occur because the ions cannot return toward the ion source against the flow of gas, and the ions cannot flow with the gas out of the grid 85 because of the confining action of the electric fields near he terminus 82T of the inner electrode. As long as the following conditions are maintained this trap will exist: (1) the DV and CV must be applied, and the voltages remain appropriate for the ion being trapped; (2) the voltages on the outer electrode and the grid remain fixed, e.g. near 0 V, as appropriate for the ion being trapped; and (3) the gas flow is maintained. If any condition changes the ions may leave the trap. If it is desired to have the ions travel to the sampler cone 18A of the mass spectrometer after passing out of the trapping region, and through the grid 85 as shown in FIG. 13C, then one of the above conditions may be optionally changed to achieve this result. This could occur in a number of ways:

(1) The grid 85 voltage may be dropped (from its value during trapping) relative to the inner electrode 82, and relative to the outer electrode 83. This will have the effect of attracting (positively charged ions) away from the FAIMS trapping region (near the terminus 82T), and thereby breaking the hold of the trap. The ions will leave the trap, and travel toward the grid 85. Some ions will strike the grid wires, and some will travel through (assisted by the gas flow). Since all of the voltages in the device must be considered relative to each other, somewhat the same effect can be achieved by changes in the voltages applied to the outer electrode 83, and to the inner electrode 82. For example, an increase in voltage applied to both the outer electrode 83 and to the inner electrode 82, will have the same effect as a decrease in the voltage applied to the grid 85.

(2) The DV or CV can be changed in many ways which alter the ion motion in the vicinity of the FAIMS trapping region. If the CV is made more negative the ions (positive ions) will tend to collide with the inner electrode 82, and if the CV is more positive the ions will be positioned farther from the inner electrode 82, and at some voltage the FAIMS trap will no longer exist for this ion and the ion will travel with the gas flow and under the influence of the average dc electric field, to the grid, as noted in (1) above. If DV is removed the trap will no longer function. If CV is altered, e.g. more positive, and DV is removed (positively charged) ions will be repelled from the inner electrode 82, and may travel to the grid.

(3) The gas flow can be changed. If the gas flow is sufficiently high to overcome the trapping action of the electric fields near the closed end of the inner electrode 82T, the ions will be pushed out of the trap and toward the grid 85, as described above. If the gas flow is decreased or stopped, the ions will move via diffusion, and via chemical changes. The diffusion will permit the ions to return back toward the ion source, thereby depopulating the FAIMS trapping region near the terminus 92T of the inner electrode 82. Even in the presence of gas flows the ions may soon depopulate the trap because of chemical effects. If the ion collides with a neutral molecule and temporarily forms a stable complex, this complex may drift out of the FAIMS trapping region because this new complex has high field mobility properties which were different from the original ion. This means that the complex may have behaviour at high electric field (see FIG. 1) which differs from the original simple parent ion. For example (at the extreme) the original ion may be of type A, and the new complex of the type C shown in FIG. 1. If this is the case, the new complex will not be trapped at the prevailing DV and CV conditions. The collision of any of these ions with the walls of the device will soon result in loss of the ions from the trap. Although the original ion itself may continue to be trapped, the removal of this ion via "chemical" effects is entirely possible, and is the reason the FAIMS analyzer will fail in the presence of water vapour or contaminants in the gas flows. The FAIMS analyzer works best in very clean conditions.

Figure 14A:
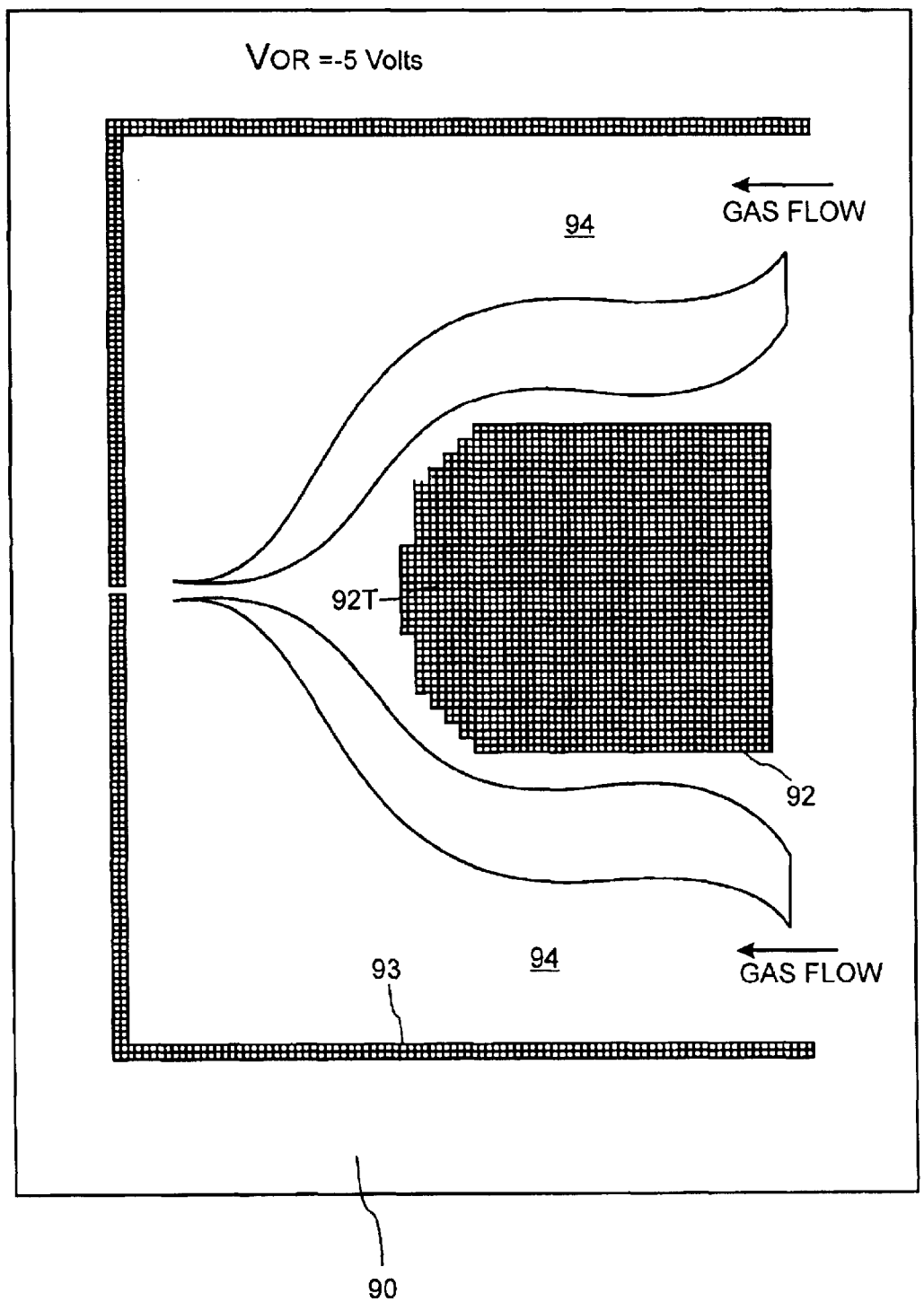
FIGS. 14A–14C illustrate various ion trajectory calculations near the curved terminus of an inner electrode.
Figure 14B:
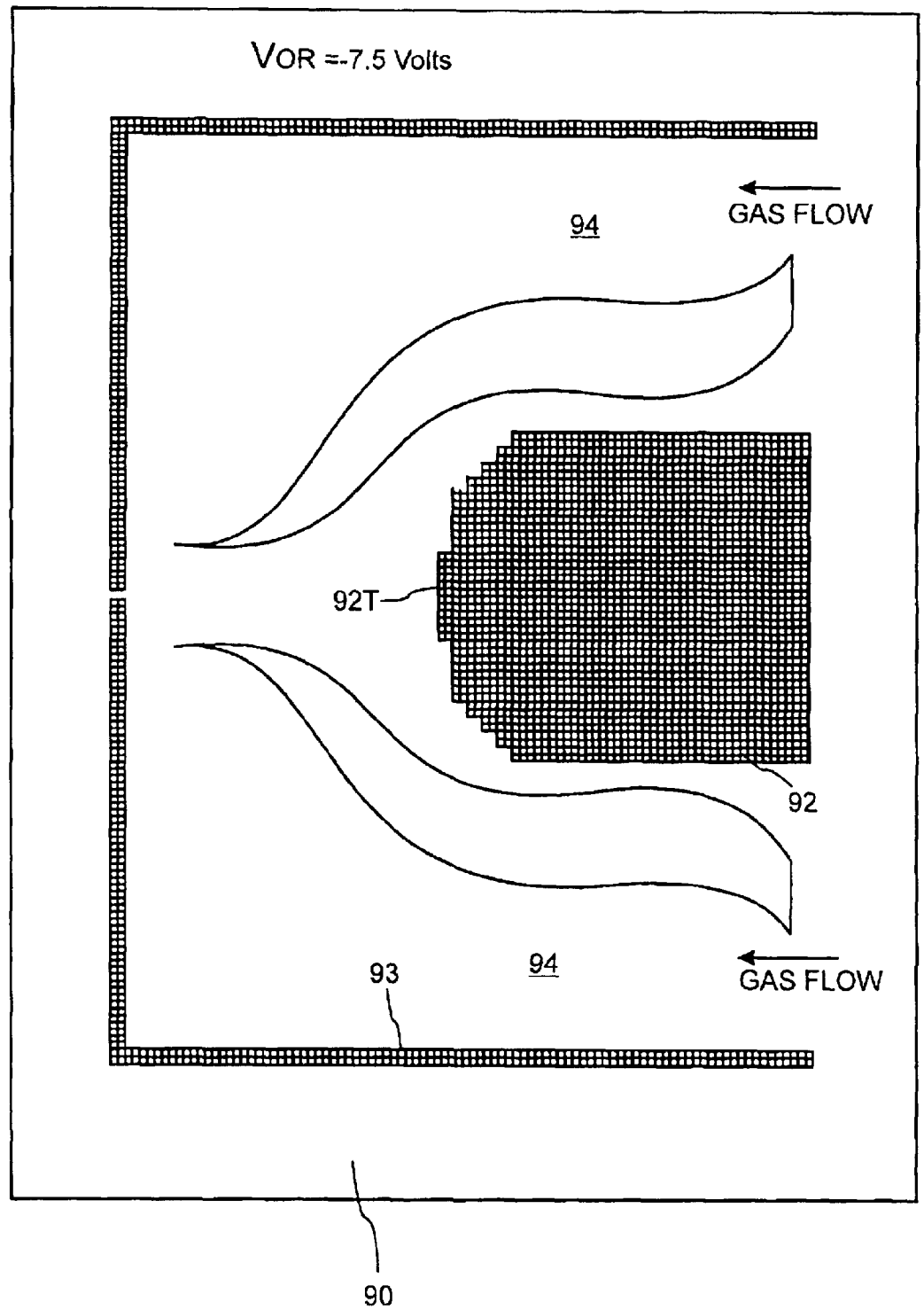
Figure 14C:
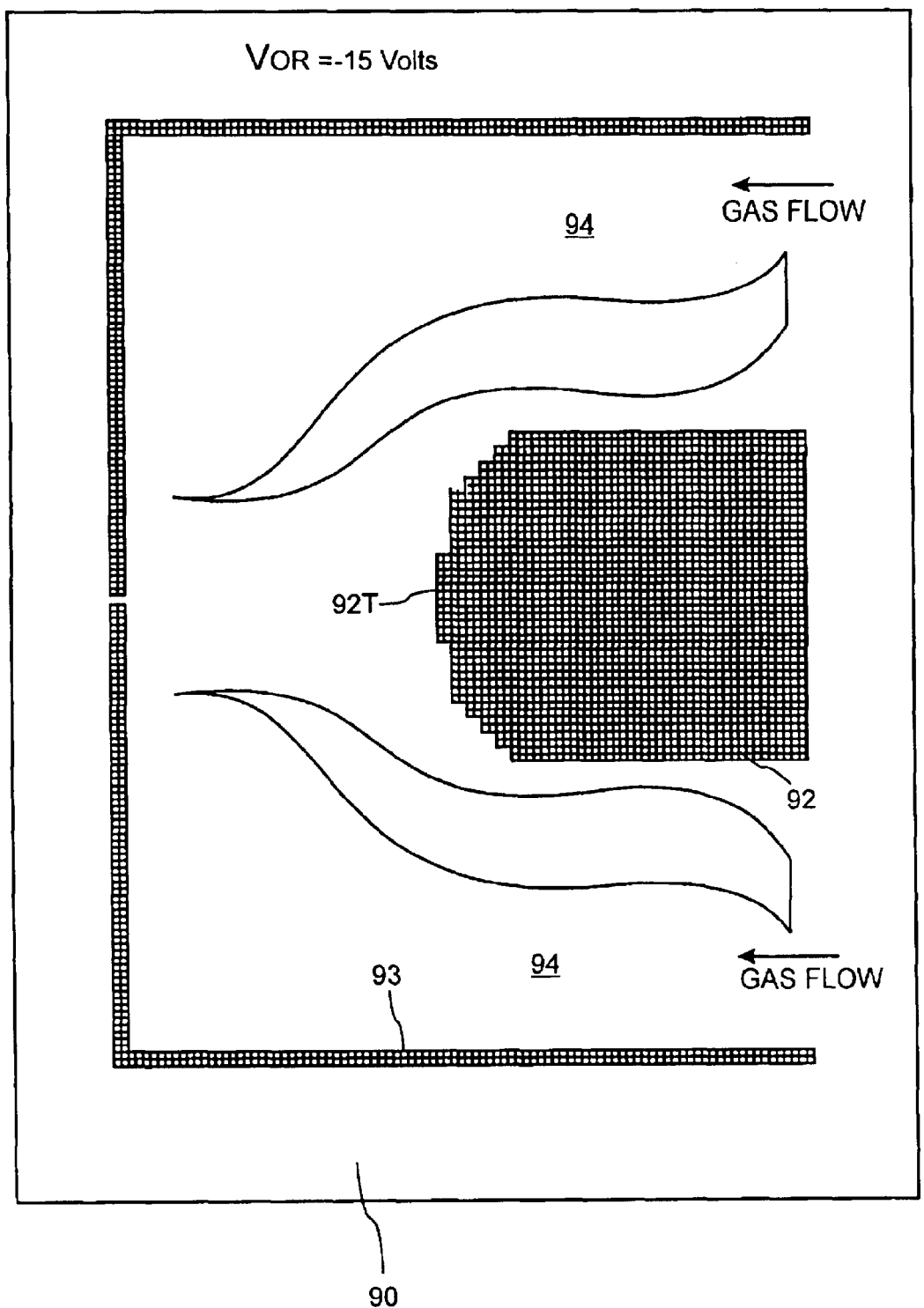

Still referring to FIGS. 13A–13C, when conditions are set such that an apparatus for 3-dimensional ion trapping is operated in a compromised condition, i.e., very near trapping conditions, the ions shown in FIG. 13B will not be trapped near the curved surface of the spherical end 52T of the electrode, but will still tend to move toward the center axis as they move from right to left In the figure. This is shown in FIGS. 14A–14C where the flow of ions progressively widen around the center axis of the FAIMS device as conditions progressively change from the very near trapping conditions shown in FIG. 14A. Advantageously, the focusing action shown in FIGS. 14A–14C, and particularly in FIG. 14A, acts to enhance the efficiency of sporting ions from the analyzer region of the FAIMS device into the sampling orifice of a mass spectrometer.

Although the invention has been described and illustrated with reference to specific embodiments, those skilled in the art will recognize that the invention may be otherwise embodied within the scope of the following claims.

We claim:

1. An apparatus for selectively transmitting and determining the mass to charge ratio of ions, comprising:
   at least one ionization source for producing ions;
   a high field asymmetric waveform ion mobility spectrometer, comprising:
   i) an analyzer region defined by a space between first and second spaced apart electrodes, said analyzer region having a gas inlet at a first end and a gas outlet at a second end for providing a flow of gas through said analyzer region, said analyzer region having an ion inlet and an ion outlet, said ion inlet for introducing a flow of ions produced by said ionization source into said analyzer region and said ion outlet for supporting extraction of ions from said analyzer region;
   ii) an electrical controller connectable to said electrodes and capable of applying an asymmetric waveform voltage and a direct-current compensation voltage to selectively transmit a type of ion in said analyzer region between said electrodes at a given combination of asymmetric waveform voltage and compensation voltage; and
   iii) a mass spectrometer having a sampler orifice, said sampler orifice being positioned proximate to said ion outlet to receive said selectively transmitted ions for analysis within said mass spectrometer,
   wherein, said first and second electrodes comprise curved electrode bodies and provide a non-constant electric field therebetween, said ions being selectively focussed in a focussing region created between said curved electrode bodies in said analyzer region.

2. The apparatus recited in claim 1, wherein, said first and second electrodes comprise outer and inner generally cylindrical coaxially aligned electrode bodies with a generally annular space formed between them, said annular space defining said analyzer region.

3. The apparatus recited in claim 1, wherein, said gas outlet and said ion outlet are substantially aligned with said focussing region at said second end.

4. The apparatus recited in claim 1, wherein said ion outlet is located on said outer electrode body proximate to said second end, said sampler orifice being positioned proximate to said ion outlet to receive said selectively focussed ions.

5. The apparatus in claim 2, wherein said generally cylindrical inner electrode body has a curved surface terminus proximate to said second end, said ion outlet being axially aligned with said inner electrode body, said asymmetrical waveform voltage, compensation voltage, and said gas flow being adjustable, whereby, said focussed ions tend to follow the curved surface of said terminus and are directed radially inwardly towards said ion outlet.

6. The apparatus in claim 5, wherein, said outer electrode body forms a curved surface which substantially follows the curved surface of said terminus, so as to maintain a substantially constant distance between said inner and outer electrodes at said second end.

7. The apparatus recited in claim 2, wherein:
   a) said ionization source is an electrospray ionizer for producing ions from a sample in liquid phase; and
   b) at least a portion of said gas flow is counter-current to said flow of ions being introduced at said ion inlet into said analyzer region, whereby, in use, said counter-current gas flow reduces the level of solvation of said flow of ions being introduced into said analyzer region.

8. The apparatus recited in claim 2, wherein, sad ionization source is coaxially aligned with said electrodes and positioned external to said inner electrode body, whereby, in use, said flow of ions are evenly directed into said generally annular shaped analyzer region in a radial fashion.

9. The apparatus recited in claim 2, further comprising a generally cylindrical ionization chamber housing said ionization source, said ionization chamber being axially aligned with said inner electrode, said ion inlet comprising a gap between said ionization chamber and said inner electrode.

10. The apparatus recited in claim 7, wherein said ion inlet is located in said outer electrode wall for introduction of said ions into said analyzer region.

11. The apparatus recited in claim 10, further comprising an ionization chamber housing said ionization source, said ionization chamber being provided with a second gas outlet for allowing said counter-current gas flow to exit.

12. The apparatus recited in claim 10, further comprising an ionization chamber housing said ionization source, and a purge gas chamber positioned between said ionization chamber hours and said ion inlet, said purge gas chamber providing a purge gas flow for desolvating said ions entering said ion inlet.

13. An apparatus for desolvating and selectively transmitting ions, comprising:
   a) at least one electrospray ionization source for producing ions from a sample in liquid phase;
   b) a high field asymmetric waveform ion mobility spectrometer, comprising:
   i) an analyzer region defined by a space between first and second spaced apart electrodes, said analyzer region being in communication with a gas inlet, a gas outlet, an ion inlet and an ion outlet, said ion inlet introducing a flow of said ions into said analyzer region, and said ion outlet allowing extraction of ions from said analyzer region;
   ii) a source of gas for providing a gas flow into said gas inlet and within said analyzer region, and out of said gas outlet, at least some of the gas flow being counter-current to said flow of ions being introduced at said ion inlet; and
   iii) an electrical controller connectable to said electrodes and capable of applying an asymmetric waveform voltage and a direct-current compensation voltage to selectively transmit a type of ion in an analyzer region between said electrodes at a given combination of asymmetric waveform voltage and compensation voltage.

14. The apparatus recited in claim 13, further comprising a mass spectrometer having a sampler cone with a sampler orifice, said sampler orifice being positioned proximate to said ion outlet so as to receive said selectively transmitted ions.

15. The apparatus recited in claim 13, wherein, said first and second electrodes comprise curved electrode bodies and provide a non-constant electric field therebetween, said ions being selectively focussed in a focussing region created between said curved electrode bodies in said analyzer region.

16. The apparatus recited in claim 13, wherein, said first and second electrodes comprise outer and inner generally cylindrical coaxially aligned electrode bodies with a generally annular space formed between them, said annular space defining said analyzer region.

17. An apparatus for selectively fitting ions, comprising:
a) at least one electrospray ionization source for producing ions from a sample in liquid phase; and
b) a high field asymmetric waveform ion mobility spectrometer, comprising:
i) an analyzer region defined by a space between first and second spaced apart electrodes, said analyzer region being in communication with a gas inlet and a gas outlet for providing, in use, a gas flow through said analyzer region, an ion inlet and an ion outlet, said ion inlet introducing a flow of ions produced by said electrospray ionization source into said analyzer region, and said ion outlet allowing extraction of ions from said analyzer region; and
ii) an electrical controller connectable to said electrodes and capable of applying an asymmetric waveform voltage and a direct-current compensation voltage to selectively transmit a type of ion in an analyzer region between said electrodes at a given combination of asymmetric waveform voltage and compensation voltage;
wherein, said electrospray ionization source is positioned external to said inner electrode so as reduce the effect of said asymmetric waveform voltage on said electrospray ionization source.

18. The apparatus recited in claim 17, wherein, said first and second electrodes comprise curved electrode bodies and provide a non-constant electric field therebetween, said ions being selectively focussed in a focussing region created between said curved electrode bodies in said analyzer region.

19. The apparatus recited in claim 17, wherein, said first and second electrodes comprise outer and inner generally cylindrical coaxially aligned electrode bodies with a generally annular space formed between them, said annular space defining said analyzer region.

20. The apparatus recited in claim 19, wherein, said ionization source is coaxially aligned with said electrodes whereby, in use, said flow of ions are evenly directed into said generally annular shaped analyzer region in a radial fashion.

21. The apparatus recited in claim 19, wherein said ion inlet is located in said outer electrode wall for introduction of said ions into said analyzer region.

22. A method for desolvating and selectively focussing ions produced by electrospray ionization for introduction into a mass spectrometer, comprising the steps of:

a) providing at least one electrospray ionization source for producing ions from a sample in liquid phase;
b) providing an analyzer region defined by a space between first and second spaced apart electrodes, said analyzer region being in communication with a gas inlet, a gas outlet, an ion inlet and an ion outlet;
c) providing a gas flow into said gas inlet, and within said analyzer region, and out of said carrier gas outlet, at least some of said gas flow being counter-current to ions being introduced at said ion inlet;
d) providing an electrical controller connectable to said electrodes and capable of applying an asymmetric waveform voltage and a direct-current compensation voltage, to at least one of said electrodes;
e) adjusting said asymmetric waveform voltage and said compensation voltage to selectively focus a type of ion; and
f) extracting said selectively transmitted ions from said analyzer region at said ion outlet for introduction into a sampler cone of a mass spectrometer.

23. An apparatus for desolvating and selectively transmitting ions, comprising:
a) at least one ionization source for producing ions;
b) a high field asymmetric waveform ion mobility spectrometer, comprising:
i) an analyzer region defined by a space between at least first and second spaced apart electrodes, said analyzer region being in communication with at least one of each of a gas inlet, a gas outlet, an ion inlet and an ion outlet, said ion inlet for introducing a flow of said ions into said analyzer region, and said ion outlet for allowing extraction of said ions from said analyzer region;
ii) at least one source of gas for providing a gas flow into said gas inlet, a gas flow through said analyzer region, a gas flow out of said gas outlet, and a gas flow being which is flowing counter-current to said flow of ions being produced by said ion source so as to desolvate said flow of ions entering said ion inlet;
iii) an electrical controller connectable to said electrodes and capable of applying an asymmetric waveform voltage and a direct-current compensation voltage to selectively transmit a type of ion in said analyzer region between said electrodes at a given combination of asymmetric waveform voltage and compensation voltage; and,
iv) a terminus provided on at least one of said electrodes and shaped for directing said ions generally radially inwardly toward said ion outlet, said terminus being a part of said one of said electrodes which part is closest to said ion outlet.

24. The apparatus claimed in claim 23, wherein, said space between said electrodes defining said analyzer region is generally uniform.

25. The apparatus claimed in claim 24, wherein said terminus is tapered toward said ion outlet.

26. The apparatus claimed in claim 25, wherein, said terminus is provided with a curved surface.

27. The apparatus claimed in claim 26, wherein, said curved surface is substantially a portion of a sphere.

28. The apparatus recited in claim 26, further comprising a mass spectrometer having a sampler orifice, said sampler orifice being positioned proximate to said ion outlet to receive said selectively transmitted ions for analysis within said mass spectrometer.

29. The apparatus recited in claim 26, wherein, said first and second electrodes comprise curved electrode bodies and provide a non-constant electric field therebetween, said ions being selectively focused in a focusing region created between said curved electrode bodies in said analyzer region.

30. The apparatus recited in claim 26, wherein, said first and second electrodes comprise outer and inner generally cylindrical coaxially aligned electrode bodies with a generally annular space formed between them, said annular space defining said analyzer region.

31. The apparatus in claim 30, wherein, said generally cylindrical inner electrode body has a curved surface terminus proximate to said ion outlet, said ion outlet being axially aligned with said inner electrode body, said asymmetric waveform voltage, compensation voltage, and said gas flow being adjustable, whereby, said focused ions tend to follow the curved surface of said terminus and are directed generally radially inwardly towards said ion outlet.

32. The apparatus claimed in claim 31, wherein, said terminus is relatively moveable to the ion outlet.

33. The apparatus in claim 32, wherein, said outer electrode body forms a curved surface which substantially follows the curved surface of said terminus, so as to maintain a substantially constant distance between said inner and outer electrodes at said cured terminus.

34. The apparatus recited in claim 30, wherein, said ionization source is coaxially aligned with said electrodes and positioned external to said inner electrode body, whereby, in use, said flow of ions are evenly directed into said generally annular shaped analyzer region in a radial fashion.

35. The apparatus recited in claim 30, further comprising a generally cylindrical ionization chamber housing said ionization source, said ionization chamber being axially aligned with said inner electrode, said ion inlet comprising a gap between said ionization chamber and said inner electrode.

36. The apparatus recited in claim 30 wherein said ion inlet is located in said outer electrode wall for introduction of said ions into said analyzer region.

37. The apparatus recited in claim 36, further comprising an ionization chamber housing said ionization source, said ionization chamber being provided with a second gas outlet for allowing said counter-current gas flow to exit.

38. The apparatus recited in claim 37, further comprising a purge gas chamber positioned bet said ionization source and said ion inlet, said purge gas chamber providing a purge gas flow for desolvating ions entering said ion inlet.

39. The apparatus recited in claim 23, wherein said ionization source is an electospray ionizer for producing ions from a sample in liquid phase, whereby, in use, said counter-current gas flow reduces the level of solvation of said flow of ions being introduced into said analyzer region.

40. The apparatus recited in claim 33, wherein said ionization source is an electrospray ionizer for producing ions from a sample in liquid phase, whereby, in use, said counter-current gas flow reduces the level of salvation of said flow of ions being introduced into said analyzer region.

41. A method for desolvating and selectively focusing ions produced by electrospray ionization for introduction into a mass spectrometer, comprising the steps of:

a) providing at least one electrospray ionization source for producing ions including two ionic species from a sample in liquid phase;

b) providing an analyzer region defined by a space between at least first and second spaced apart electrodes, said analyzer region being in communication with at least one of each of a gas inlet, a gas outlet, an ion inlet and an ion outlet;

c) providing a terminus on at least one of said electrodes and shaped for directing said ions generally radially inwardly toward said ion outlet, said terminus being a part of said one of said electrodes which part is closest to said ion outlet, d) providing a gas flow into said gas inlet, and within said analyzer region, and out of said gas outlet, at least some gas flow being count-current to ions being produced at said ion source so as to desolvate said flow of ions entering said ion inlet;

e) providing an electrical controller connectable to said electrodes and capable of applying an asymmetric waveform voltage and a direct-current compensation voltage, to at least one of said electrodes;

f) setting said asymmetric waveform voltage in order to affect a difference in net displacement between said two ionic species in the time of one cycle of said applied asymmetric waveform voltage;

g) setting said compensation voltage to a determined value to selectively focus one of said two ionic species; and, h) extracting said selectively focused ions from said analyzer region at said ion outlet for introduction into a sampler orifice of a mass spectrometer.

42. The method claimed in claim 41, wherein said terminus is tapered toward said ion outlet.

43. The method claimed in claim 42, wherein, said terminus is provided with a curved surface.

44. The method claimed in claim 43, wherein, said curved surface is substantially a portion of a sphere.

45. The method claimed in claim 41, comprising the additional steps prior to step g) of:

f1) varying said direct current compensation voltage to compensate for some of the displacement of one of said two ionic species resulting from the applied asymmetric waveform voltage and measuring resulting transmitted ions at said ion outlet, so as to produce a compensation voltage scan for said transmitted ions of different isotopic composition;

f2) identifying peaks in said compensation voltage scan corresponding to said transmitted ions; and, f3) determining an appropriate direct current compensation voltage corresponding to one of said peaks, so as to separate and enrich said one of said two ionic species.

46. The method claimed in claim 45, comprising the additional step prior to step h) of:

g1) further adjusting at least one of said asymmetric waveform voltage, compensation voltage and gas flow so as to provide near trapping conditions, whereby, said focused ions tend to follow the curved surface of said terminus and are directed generally radially inwardly towards said ion outlet.

* * * * *